(12) United States Patent
Chu et al.

(10) Patent No.: US 9,717,721 B2
(45) Date of Patent: Aug. 1, 2017

(54) USE OF ARYL-QUINOLIN DERIVATIVES AS INHIBITORS OF VASCULOGENIC MIMICRY

(71) Applicant: TaiRx Inc., Taipei (TW)

(72) Inventors: Yi-Wen Chu, New Taipei (TW); Du-Shieng Chien, Guilford, CT (US)

(73) Assignee: TAIRX, INC., Taipei (TW)

( * ) Notice: Subject to any disclaimer, the term of this patent is extended or adjusted under 35 U.S.C. 154(b) by 0 days.

(21) Appl. No.: 15/171,365

(22) Filed: Jun. 2, 2016

(65) Prior Publication Data

US 2016/0354361 A1   Dec. 8, 2016

Related U.S. Application Data

(60) Provisional application No. 62/170,425, filed on Jun. 3, 2015.

(51) Int. Cl.
| | | |
|---|---|---|
| *A61K 31/47* | (2006.01) | |
| *A61K 31/675* | (2006.01) | |
| *A61K 31/4741* | (2006.01) | |
| *A61K 31/685* | (2006.01) | |
| *A61K 31/4709* | (2006.01) | |
| *A61K 31/5377* | (2006.01) | |

(52) U.S. Cl.
CPC .......... *A61K 31/47* (2013.01); *A61K 31/4709* (2013.01); *A61K 31/4741* (2013.01); *A61K 31/5377* (2013.01); *A61K 31/675* (2013.01); *A61K 31/685* (2013.01)

(58) Field of Classification Search
CPC .. A61K 31/47; A61K 31/675; A61K 31/5377; A61K 31/685; A61K 31/4709; A61K 31/4741
See application file for complete search history.

(56) References Cited

U.S. PATENT DOCUMENTS

| | | | |
|---|---|---|---|
| 8,524,740 B2* | 9/2013 | Kuo .................... | C07D 215/22 514/291 |
| 2010/0168064 A1* | 7/2010 | Kuo .................... | C07D 421/04 514/81 |

* cited by examiner

*Primary Examiner* — Sudhakar Katakam
(74) *Attorney, Agent, or Firm* — Hsiu-Ming Saunders; Intellectual Property Connections, Inc.

(57) ABSTRACT

Aryl-quinolin derivatives for use in inhibiting vasculogenic mimicry, treating diseases characterized by abnormal vascular morphology or function and/or by the presence of vasculogenic mimicry in a subject in need thereof are disclosed. In one embodiment of the invention, the compounds are for use in treating metastatic tumor, hyperproliferative, or angiogenic diseases. In another embodiment of the invention, the compound for use may combine an additional therapeutic agent such as anti-cancer agents, anti-inflammatory agents, anti-proliferative agents, anti-hormonal agents, or any combination thereof for use.

9 Claims, 6 Drawing Sheets

USE OF ARYL-QUINOLIN DERIVATIVES AS INHIBITORS OF VASCULOGENIC MIMICRY

REFERENCE TO RELATED APPLICATION

The present application claims the priority to U.S. Provisional Application Ser. No. 62/170,425, filed Jun. 3, 2015, which is herein incorporated by reference in its entirety.

FIELD OF THE INVENTION

The invention relates to a novel use of aryl-quinolin derivatives and more specifically to aryl-quinolin derivatives for use in inhibiting vasculogenic mimicry and treating diseases or conditions associated with aberrant vessel morphology and function and/or characterized by the presence of vasculogenic mimicry.

BACKGROUND OF THE INVENTION

The term vasculogenic mimicry describes the formation of fluid-conducting channels by highly invasive and genetically dysregulated tumor cells. Two distinctive types of vasculogenic mimicry have been described. Vasculogenic mimicry of the tubular type may be confused morphologically with endothelial cell-lined blood vessels. Vasculogenic mimicry of the patterned matrix type in no way resembles blood vessels morphologically or topologically. Matrix proteins such as laminin, heparan sulfate proteoglycan, and collagens IV and VI have been identified in these patterns. The patterned matrix anastomoses with blood vessels.

Vasculogenic mimicry of the patterned matrix type has been identified in uveal, cutaneous and mucous membrane melanomas, inflammatory and ductal breast carcinoma, ovarian and prostatic carcinoma, lung carcinoma, renal carcinoma, hepatocellular carcinoma, mesothelial sarcoma, bladder carcinoma, osteosarcoma, astrocytoma, pheochromocytoma, colorectal cancer, medulloblastoma, adenocarcinoma, esophageal stromal tumors, gestational choriocarcinoma, gallbladder carcinoma, gastrointestinal cancer, laryngeal cancer, synoviosarcoma, glioblastoma, leukemia and soft tissue sarcomas, including synovial sarcoma rhabdomyosarcoma, osteosarcoma, Ewing sarcoma, and pheochromocytoma.

Evidence shows that vasculogenic mimicry plays a role in aggressive metastasis in laryngeal squamous cell carcinoma, hepatocellular carcinoma, renal cell carcinoma, breast cancer, ovarian carcinoma, primary gallbladder carcinoma, malignant esophageal stromal carcinoma, hepatocellular carcinoma, mesothelial sarcoma and alveolar rhabdomyosarcoma. Individuals with melanomas that exhibit VM have poor prognosis and a higher risk of cancer recurrence. Inhibitors of VM may be used to block metastasis or slow down tumor growth. Therefore, it has been postulated that antagonizing agents of VM formation may have beneficial effects in inhibiting tumor growth and highly aggressive metastasis.

WO 2012/009519 discloses synthesis and anticancer activity of aryl and heteroaryl-quinolin derivatives.

SUMMARY OF THE INVENTION

In one aspect the invention relates to a compound of formula I, II, III, or IV as follows, or a pharmaceutically acceptable salt thereof, for use in inhibiting vasculogenic mimicry in a subject in need thereof:

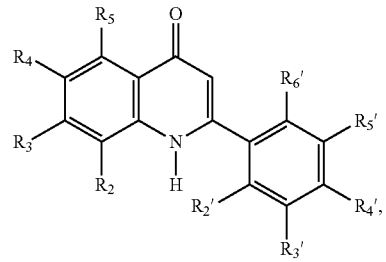

wherein $R_2'$, $R_3'$, $R_4'$, $R_5'$ and $R_6'$ independently are H, $(CH_2)_nCH_3$, $(CH_2)_nYH$, $Y(CH_2)_nCH_3$, $Y(CH_2)_nYH$, $Y(CH_2)_nNR_8R_9$, X, or $(CH_2)_nNR_8R_9$, or $R_3'=OP(=O)(O\text{-benzyl})_2$, wherein n is an integer of 0-4, Y is O or S, X is F, Cl, or Br, and $R_8$ and $R_9$ independently are H, $(CH_2)_nYH$, $(CH_2)_nN(C_nH_{2n+1})(C_mH_{2m+1})$ or $(CH_2)_nCH_3$, wherein n and Y are defined as above, and m is an integer of 0-4;

$R_2$, $R_3$, $R_4$ and $R_5$ independently are H, $(CH_2)_nCH_3$, $(CH_2)_nYH$, $Y(CH_2)_nCH_3$, $Y(CH_2)_nYH$, $Y(CH_2)_nNR_8R_9$, X, $(CH_2)_nNR_8R_9$, $(CH_2)_nN$, or $R_4$ and $R_5$ together is —Y$(CH_2)_nY$—, or $R_3$ and $R_4$ together is —Y$(CH_2)_nY$—, wherein n, Y, X, $R_8$ and $R_9$ are defined as above, or $R_3$ is O-benzyl; and $R_1$ and $R_1'$ independently are H, Li$^+$, Na$^+$, K$^+$, Ca$^{++}$, Mg$^{++}$, N$^+R_8R_9R_{10}R_{11}$ or benzyl wherein $R_{10}$ and $R_{11}$ independently are H, $(CH_2)_nYH$, $(CH_2)_nN(C_nH_{2n+1})(C_mH_{2m+1})$ or $(CH_2)_nCH_3$, n, m, $R_8$ and $R_9$ are as defined above.

In one embodiment of the invention, $R_2'$, $R_3'$, $R_4'$, $R_5'$ and $R_6'$ are all H; or one of $R_2'$, $R_3'$, $R_4'$, $R_5'$ and $R_6'$ is F, $OCH_3$ or $(CH_2)_nNR_8R_9$, and the others thereof are H, wherein n, $R_8$ and $R_9$ are as defined above.

In another embodiment of the invention, $R_2$, $R_3$, $R_4$, and $R_5$ are all H; or one of $R_2$, $R_3$, $R_4$, and $R_5$ is F, $OCH_3$, $Y(CH_2)_nCH_3$ or $(CH_2)_nNR_8R_9$, and the others thereof are H; or $R_2$ and $R_5$ are H, and $R_3$ and $R_4$ together is —$O(CH_2)_nO$—, wherein n, Y, $R_8$ and $R_9$ are as defined above.

In another embodiment of the invention, $R_1$ and $R_1'$ are H, $Na^+$, and/or $K^+$.

In another embodiment of the invention, $R_2$ and $R_5$ are H, and $R_3$ and $R_4$ together is —$O(CH_2)O$—; and $R_2'$, $R_3'$, $R_4'$, and $R_5'$ are all H, and $R_6'$ is F.

In another embodiment of the invention, $R_2$ and $R_5$ are H, and $R_3$ and $R_4$ together is —$O(CH_2)O$—; and $R_2'$, $R_3'$, $R_4'$ and $R_6'$ are all H, and $R_5'$ is F.

In another embodiment of the invention, $R_2$, $R_3$, $R_4$ and $R_5$ are H, and $R_2'$, $R_3'$, $R_4'$, $R_5'$ and $R_6'$ are all H.

In another embodiment of the invention, $R_4$ is $OCH_3$, and $R_2$, and $R_3$ and $R_5$ are H; and $R_5'$ is F, and $R_2'$, $R_3'$, $R_4'$, and $R_6'$ are H.

In another embodiment of the invention, $R_2$ and $R_5$ are H, and $R_3$ and $R_4$ together is —$O(CH_2)O$—; and $R_2'$, $R_3'$, $R_4'$, and $R_6'$ are all H, and $R_5'$ is $OCH_3$.

In another embodiment of the invention, the compound is at least one selected from the group consisting of compound Nos. 38, 43, 52, 147, A6, B1, B3, C4, and C6.

In another embodiment of the invention, the subject is suffering from a disease characterized by abnormal vascular morphology or function and/or by the presence of vasculogenic mimicry.

Further in another embodiment of the invention, the disease is at least one selected from the group consisting of metastatic tumors, hyperproliferative disorders, inflammatory diseases, and ophthalmological diseases.

The metastatic tumor may be at least one selected from the group consisting of melanoma, ovarian cancer, prostate cancer, renal cell carcinoma, Ewing sarcoma, breast cancer, neuroendocrine carcinoma, thyroid carcinoma, laryngeal squamous cell carcinoma, hepatocellular carcinoma, uveal melanoma, cutaneous melanoma, oral malignant melanoma, choriocarcinoma, primary gallbladder cancer, malignant esophageal stromal carcinoma, mesothelial sarcoma, alveolar rhabdomyosarcoma, bladder cancer, osteosarcoma, astrocytoma, pheochromocytoma, colorectal cancer, medulloblastoma, adenocarcinoma, esophageal stromal tumors, laryngeal cancer, leukemia, synoviosarcoma, glioblastoma, and gastrointestinal cancer.

The hyperproliferative disorder may be at least one selected from the group consisting of disorders of psoriatic arthritis, rheumatoid arthritis, lupus, reactive arthritis, Sjogren's disease, inflammatory bowel disorder, dermatomyositis, ankylosing spondylitis, juvenile rheumatoid arthritis, gout, inflammatory osteoarthritis, pseudogout, amyloidosis, keratinization and keratosis, diabetic retinopathy, endometriosis, macular degenerative disorders, keloids, warts, cirrhosis, chronic inflammatory-related disorders, proliferative vitreoretinopathy, retinopathy of prematurity, granulomatosis, immune hyperproliferation associated with organ, or tissue transplantation, benign prostatic hypertrophy, and an immunoproliferative disease or disorder.

The inflammatory disease may be at least one selected from the group consisting of acne vulgaris, Alzheimer's, arthritis, asthma, atherosclerosis, autoimmune diseases, celiac disease, chronic prostatitis, colitis, Crohn's disease, dermatitis, diverticulitis, glomerulonephritis, hepatitis, inflammatory bowel diseases, interstitial cystitis, irritable bowel syndrome, lupus erythematous, nephritis, Parkinson's disease, pelvic inflammatory disease, rheumatoid arthritis, sarcoidosis, transplant rejection, ulcerative colitis, and vasculitis.

The ophthalmological disease may be at least one selected from the group consisting of age-related macular degeneration (AMD), proliferative diabetic retinopathy (PDR), diabetic macular edema (DME), central retinal vein occlusion (CRVO), neovascular glaucoma, corneal neovascularization (trachoma), and pterygium.

In another aspect, the invention relates to a compound of Formula Ia or Ib as follows, or a pharmaceutically acceptable salt thereof for use in inhibiting, reducing, and/or alleviating vasculogenic mimicry in a subject in need thereof:

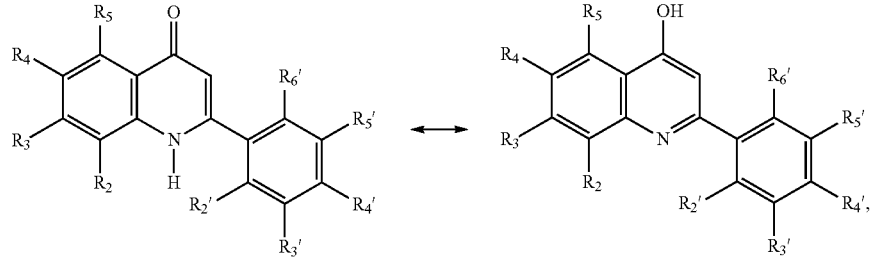

Formula Ia        Formula Ib wherein
$R_2'$, $R_3'$, $R_4'$, $R_5'$, $R_6'$ are independently H, F, Cl, Br, $(CH_2)_nCH_3$, $(CH_{2n})OH$, O—$(CH_2)_nCH_3$, $O(CH_2)_nOH$, $(CH_{2n})SH$, S—$(CH_2)_nCH_3$, $S(CH_2)_nSH$, $O(CH_2)_nSH$, $S(CH_2)_nOH$, $(CH_2)_nNR_8R_9$, $O(CH_2)_nNR_8R_9$, or $S(CH_2)_nNR_8R_9$, or $R_3'$=$OP(=O)(O$-benzyl$)_2$, and wherein $R_8$ and $R_9$ are independently H, $(CH_2)_nCH_3$, $(CH_{2n})OH$, $(CH_{2n})SH$, $(CH_2)_nN(C_nH_{2n+1})(C_mH_{2m+1})$ and n and m are each integers of 0-4;

$R_2$, $R_3$, $R_4$ and $R_5$ are independently H, F, Cl, Br, $(CH_2)_nCH_3$, $(CH_2)_nOH$, $O(CH_2)_nCH_3$, $O(CH_2)_nOH$, $O(CH_2)_nNR_8R_9$, $(CH_2)_nSH$, $S(CH_2)_nCH_3$, $S(CH_2)_nSH$, $S(CH_2)_nNR_8R_9$, $(CH_2)_nNR_8R_9$, $(CH_2)_nN$, or $R_4$ and $R_5$ together is —$O(CH_2)_nO$—, or —$S(CH_2)_nS$—, or $R_3$ and $R_4$ together is —$O(CH_2)_nO$—, or —$S(CH_2)_nS$—, wherein n, $R_8$ and $R_9$ are as defined above, or $R_3$ is O-benzyl;

or $R_5$ is OP=OO$R_1$O$R_1$ and $R_1$ and $R_1'$ are independently H, $Li^+$, $Na^+$, $K^+$, $Ca^{++}$, $Mg^{++}$, $N^+R_8R_9R_{10}R_{11}$ or benzyl, wherein $R_{10}$ and $R_{11}$ are independently H, $(CH_2)_nYH$, $(CH_2)_nN(C_nH_{2n+1})(C_mH_{2m+1})$ or $(CH_2)_nCH_3$, n, m, $R_8$ and $R_9$ are defined above.

Further in another aspect, the invention relates to a compound of Formula (X) as follows, or a pharmaceutically acceptable salt, thereof, for use in inhibiting, reducing, and/or alleviating vasculogenic mimicry in a subject in need thereof:

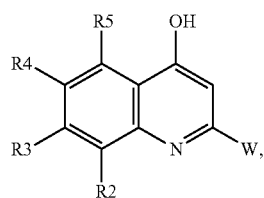

Formula (X)

wherein W is an aromatic group selected from the group consisting of naphthyl, quinolin, benzofuranyl, benzothiophene, anthracene, and substituted benzene of formula (Y):

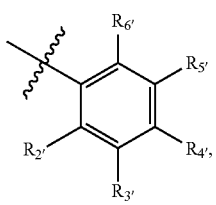

Formula (Y)

and wherein:

$R_2'$, $R_3'$, $R_4'$, $R_5'$, $R_6'$ are independently H, F, Cl, Br, $(CH_2)_nCH_3$, $(CH_{2n})OH$, $O-(CH_2)_nCH_3$, $O(CH_2)OH$, $(CH_{2n})SH$, $S-(CH_2)_nCH_3$, $S(CH_2)_nSH$, $O(CH_2)_nSH$, $S(CH_2)_nOH$, $(CH_2)_nNR_8R_9$, $O(CH_2)_nNR_8R_9$, or $S(CH_2)_nNR_8R_9$ or $R_3'=OP(=O)(O\text{-benzyl})_2$, and wherein $R_8$ and $R_9$ are independently H, $(CH_2)_nCH_3$, $(CH_{2n})OH$, $(CH_{2n})SH$, $(CH_2)_nN(C_nH_{2n+1})(C_mH_{2m+1})$ and n and m are each integers of 0-4;

$R_2$, $R_3$, $R_4$ and $R_5$ are independently H, F, Cl, Br, $(CH_2)_nCH_3$, $(CH_2)_nOH$, $O(CH_2)_nCH_3$, $O(CH_2)_nOH$, $O(CH_2)_nNR_8R_9$, $(CH_2)_nSH$, $S(CH_2)_nCH_3$, $S(CH_2)_nSH$, $S(CH_2)_nNR_8R_9$, $(CH_2)_nNR_8R_9$, $(CH_2)_nN$, or $R_4$ and $R_5$ together is $-O(CH_2)_nO-$, or $-S(CH_2)_nS-$, or $R_3$ and $R_4$ together is $-O(CH_2)_nO-$, or $-S(CH_2)_nS-$, wherein n, $R_8$ and $R_9$ are as defined above, or $R_3$ is O-benzyl;

or $R_5$ is $OP=OOR_1OR_1$ and $R_1$ and $R_1'$ are independently H, $Li^+$, $Na^+$, $K^+$, $Ca^{++}$, $Mg^{++}$, $N^+R_8R_9R_{10}R_{11}$ or benzyl, wherein $R_{10}$ and $R_{11}$ are independently H, $(CH_2)_nYH$, $(CH_2)_nN(C_nH_{2n+1})(C_mH_{2m+1})$ or $(CH_2)_nCH_3$, n, m, $R_8$ and $R_9$ are defined above.

In one embodiment of the Invention, the compound, for use is at least one selected from the group consisting of compound Nos. 16-24, 37-45, 48-53, 124-143, 143a, 143b, 144, 144a, 144b, 146-147, 152-153, 157-158, 166-169, and CHM-2133 as listed in Table 4.

Alternatively, the invention relates to use of a compound of Formula I, II, III, or IV; or Formula Ia or Ib; or Formula (X) as defined above, or a pharmaceutically acceptable salt thereof, in the manufacture of a medicament for inhibiting vasculogenic mimicry in a subject in need thereof.

The invention also relates to a method for inhibiting vasculogenic mimicry, comprising administering to a subject in need thereof a therapeutically effective amount of a compound of Formula I, II, III, or IV; or Formula Ia or Ib; or Formula (X) as defined above.

The compound of Formula I, II, III, or IV; or Formula Ia or Ib; or Formula (X) for use as defined above may combine with an additional therapeutic agent for use, in which the additional therapeutic agent is at least, one selected from the group consisting of anti-cancer agents, anti-inflammatory agents, anti-proliferative agents, anti-hormonal agents, and any combination thereof.

These and other aspects will become apparent from the following description of the preferred embodiment taken in conjunction with the following drawings, although variations and modifications therein may be affected without departing from the spirit and scope of the novel concepts of the disclosure. The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
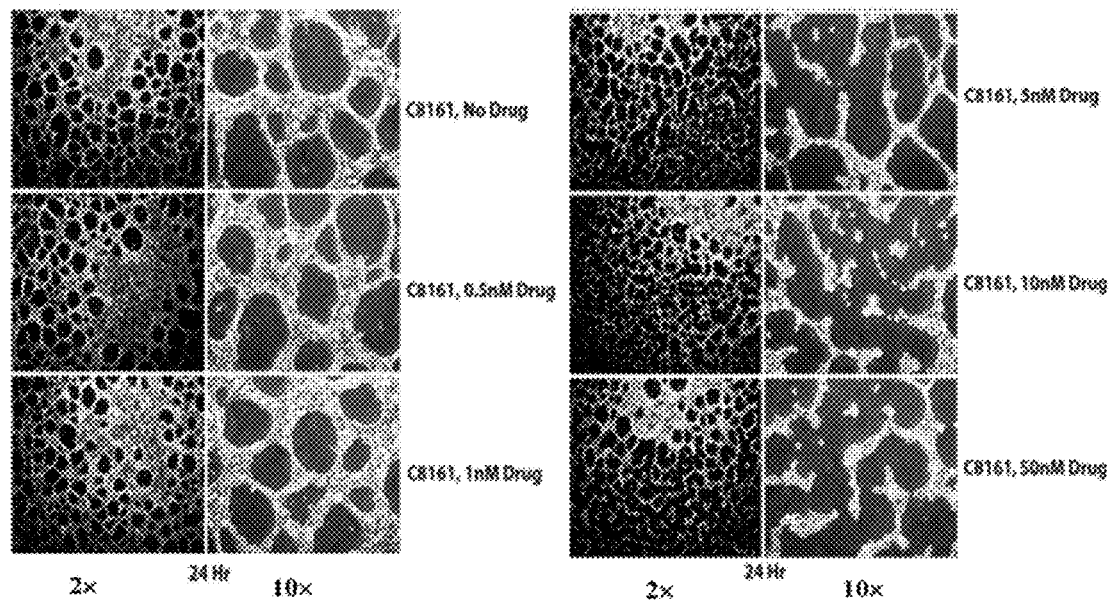
FIG. 1 shows microphotographs illustrating inhibition of VM network formation by TRX-818 in C8161 aggressive melanoma cells.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention, it will, be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. The use of examples anywhere in this specification including examples of any terms discussed herein is illustrative only, and in no way limits the scope and meaning of the invention or of any exemplified term. Likewise, the invention is not limited to various embodiments given in this specification.

The term vasculogenic mimicry describes the formation of fluid-conducting channels by highly invasive and genetically dysregulated tumor cells. The term "metastatic tumor" refers to cancers that have spread from the site of origination to another part of the body, involving abnormal formation of blood vessels and vascular channels. Without being limited thereto, metastatic tumors in the present invention include tumors that involve hypervascular metastasis, for example, melanoma, ovarian cancer, prostate cancer, renal cell carcinoma, Ewing sarcoma, breast cancer, neuroendocrine carcinoma, thyroid carcinoma, laryngeal squamous cell carcinoma, hepatocellular carcinoma, uveal melanoma, cutaneous melanoma, oral malignant melanoma, choriocarcinoma, primary gallbladder cancer, malignant esophageal stromal carcinoma, mesothelial sarcoma, alveolar rhabdomyosarcoma, bladder cancer, osteosarcoma, astrocytoma, pheochromocytoma, colorectal cancer, medulloblastoma, adenocarcinoma, esophageal stromal tumors, laryngeal cancer, leukemia, synoviosarcoma, glioblastoma, and gastrointestinal cancer.

The term "hyperproliferative disorder" refers to any disease or disorder in which the cells proliferate more rapidly than normal tissue growth. A hyperproliferating cell is a cell that is proliferating more rapidly than normal cells.

The term "inflammatory disease" refers to a condition characterized by inflammatory abnormality, and includes acne vulgaris, Alzheimer's disease, arthritis, asthma, atherosclerosis, autoimmune diseases, celiac disease, chronic prostatitis, colitis, Crohn's disease, dermatitis, diverticulitis, glomerulonephritis, hepatitis, inflammatory bowel diseases, interstitial cystitis, irritable bowel syndrome, lupus erythematous, nephritis, Parkinson's disease, pelvic inflammatory disease, rheumatoid arthritis, sarcoidosis, transplant rejection, ulcerative colitis, and vasculitis, without being limited thereto.

The term "ophthalmological disease" as used herein includes age-related macular degeneration (AMD), proliferative diabetic retinopathy (PDR), diabetic macular edema (DME), central retinal vein occlusion (CRVO), neovascular glaucoma, corneal neovascularization (trachoma), and pterygium, without limitations thereto.

An "anti-angiogenic agent" when used herein refers to a compound or composition that inhibits angiogenesis, blocking blood, vessel growth, or disrupts/removes angiogenic vessels either in vitro or in vivo. Examples of anti-angiogenic agents include VEGF/VEGFR, PDGF/PDEGFR inhibitors, steroids, kinase inhibitors, thalidomide itraconazole carboxyamidotriazole, TNP-470 CM101, IFN-α, IL-12, platelet factor-4, suramin, SU5416, thrombospondin, cartilage-derived angiogenesis inhibitory factor, matrix metalloproteinase inhibitors, angiostatin, endostatin, 2-methoxyestradiol, tecogalan, tetrathiomolybdate, thrombospondin, prolactin, $\alpha_v\beta_3$ inhibitors, linomide, tasquinimod.

The terms "chemotherapeutic agent" and "anti-cancer agent" are interchangeable. An "anti-cancer agent" refers to an agent that either inhibits the growth of cancerous cells, or causes the death of cancerous cells. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine;

urethan; vindesine; dacarbazine; mannomustsne; mitobronitol; mitolactol; pipobroman; gacytosine; arabinoside ("Ara-C"); cyclophosphamide; thiotepa; taxanes, e.g., paclitaxel, and docetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like. The aryl can optionally be a divalent radical, thereby providing an arylene.

The aryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR<x>R<y> and/or COOR<x>, wherein each R<x> and R<y> are independently H, alkyl, alkenyl, aryl, heteroaryl, heterocycle, cycloalkyl, or hydroxy.

The term "derivative or analogue" of a compound refers to a chemically modified compound wherein the chemical modification takes place at one or more functional groups of the compound and for on an aromatic, alicyclic, or heterocyclic structures, when present. The derivative or analogue however is expected to retain the pharmacological activity of the compound from which it is derived.

Concentrations, amounts, etc., of various components are often presented in a range format throughout this disclosure. The description in range format is merely for convenience and brevity and should not be construed as an inflexible limitation on the scope of the claimed invention. Accordingly, the description of a range should be considered to have specifically disclosed all the possible subranges as well as individual numerical values within that range. For example, description of a range such as 1% to 8% should be considered to have specifically disclosed subranges such as 1% to 7%, 2% to 8%, 2% to 6%, 3% to 6%, 4% to 8%, 3% to 8% etc., as well as individual numbers within that range, such as, 2%, 5%, 7% etc. This construction, applies regardless of the breadth of the range and in all contexts throughout this disclosure.

The compounds described herein are disclosed in WO 2012/009519, which is herein incorporated by reference in its entirety.

The term "treating" or "treatment" refers to administration of an effective amount of a therapeutic agent to a subject in need thereof with the purpose of cure, alleviate, relieve, remedy, ameliorate, or prevent the disease, the symptoms of it, or the predisposition towards it. Such a subject can be identified by a health care professional based on results from any suitable diagnostic method.

"An effective amount" refers to the amount of an active agent that is required to confer a therapeutic effect on the treated subject. Effective doses will vary, as recognized by those skilled in the art, depending on routes of administration, excipient usage, and the possibility of co-usage with other therapeutic treatment.

QD×28 means that animals were dosed once a day for 28 days. QOD×7 means that animals were dosed every other day for 7 doses. Q4D×3 means that animals were dosed once every 4 day for a total of 3 doses.

The term "MED" refers to "Minimum Effective Dose".

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

$$HED = \text{animal dose in mg/kg} \times (\text{animal weight in kg/human weight in kg})^{0.33}.$$

The invention relates to a novel use of aryl-quinolin derivatives and more specifically to aryl-quinolin derivatives for use in inhibiting vasculogenic mimicry and treating diseases or conditions associated with aberrant vessel morphology and function and/or characterized by the presence of vasculogenic mimicry in a subject in need thereof, in particular, the invention relates to aryl-quinolin derivatives for use in treating highly metastatic tumors, hyperproliferative disorders, inflammatory diseases, and ophthalmologicsl diseases characterized by the presence of vascular mimicry network.

The invention may be applied in combination with other anti-metastatic oncology therapies, or in combination therapies for enhancing the therapeutic effects of anti-angiogenic, chemotherapeutic, or immunotherapeutic agents in treatment of highly aggressive metastatic spread of tumor cells or other proliferative disorders.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed, and disclosed herein; however, in no way they, whether they are right or wrong, should limit the scope of the invention so long as the invention is practiced according to the invention without regard for any particular theory or scheme of action.

Example 1

TRX-818 Inhibits Vasculogenic Mimicry Network Formation in Aggressive Melanoma Cells

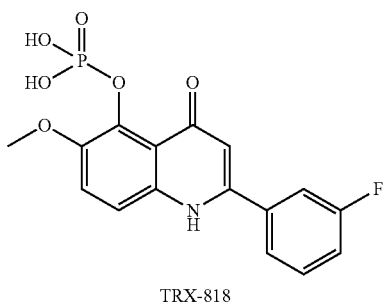

TRX-818

Solutions of TRX-818 (2-(3-fluorophenyl)-6-methoxy-4-oxo-1,4-dihydroquinolin-5-yl phosphate) were prepared as follows. TRX-818 in sodium salt form was weighed, dissolved in sterile tissue culture water to prepare a 10 mM stock solution in advance. The stock solution was then aliquoted and stored frozen until use. A fresh aliquot of the stock solution was thawed, and diluted using a cell culture medium in series to prepare the final working solution on the day of assay.

Aggressive human melanoma (C8161 or SK-MEL28; $1\times10^5$) cells were seeded into a three-dimensional polymerized MATRIGEL™ (75 µl) for VM network analysis. C8161 or SK-MEL28 cells were treated for 24 h with 0.5, 1, 5, 10, 25 or 50 or 100 nM of TRX-818 at 5 or 24 h after cell attachment. Another set of melanoma cells were seeded onto a plastic dish and treated for the same amount of time before the cell viability of C8161 or SK-MEL28 cells was determined using the Guava Nexin Assay (Millipore, USA).

The VM network image was taken using a confocal laser scanning microscope equipped with an environmental chamber to track the response of cancer cells to the test compound. The images were then digitized and subsequently analyzed using the Angiosys software. Four images per sample were analyzed to quantify the number of junctions and total tubule length of VM formation. Changes were presented in percentage relative to the vehicle control. Sterile deionized water (tissue-culture grade) was used as the vehicle control.

Figure 2:
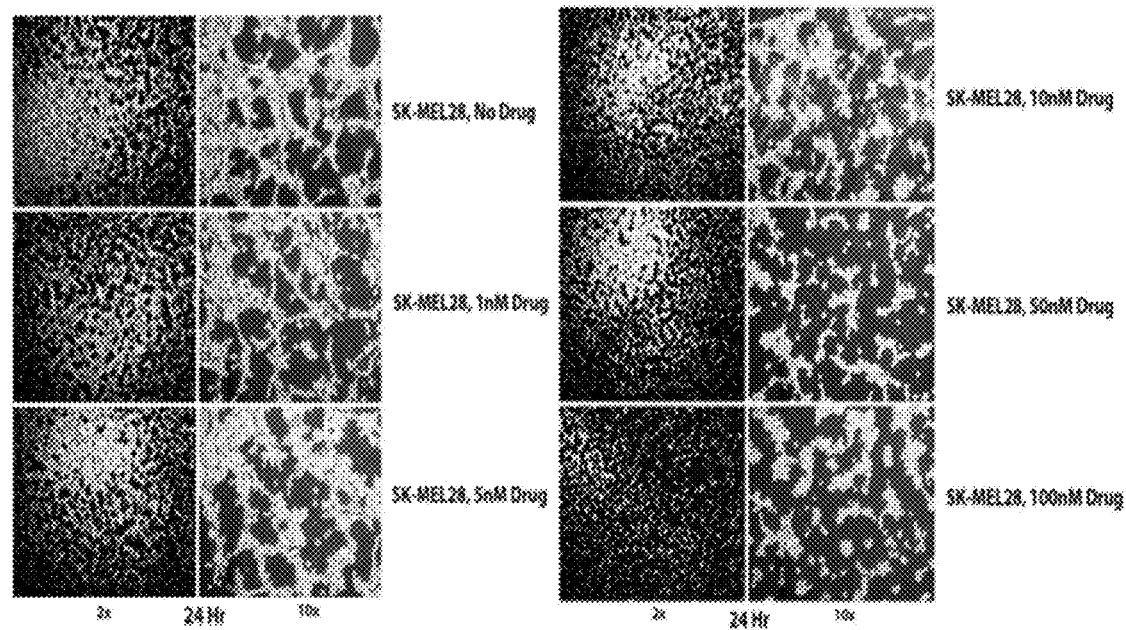
FIG. 2 shows microphotographs illustrating inhibition of VM network formation by TRX-818 at concentrations ≤5 to 10 nM in SK-MEL28 cancer cells.
Figure 3:
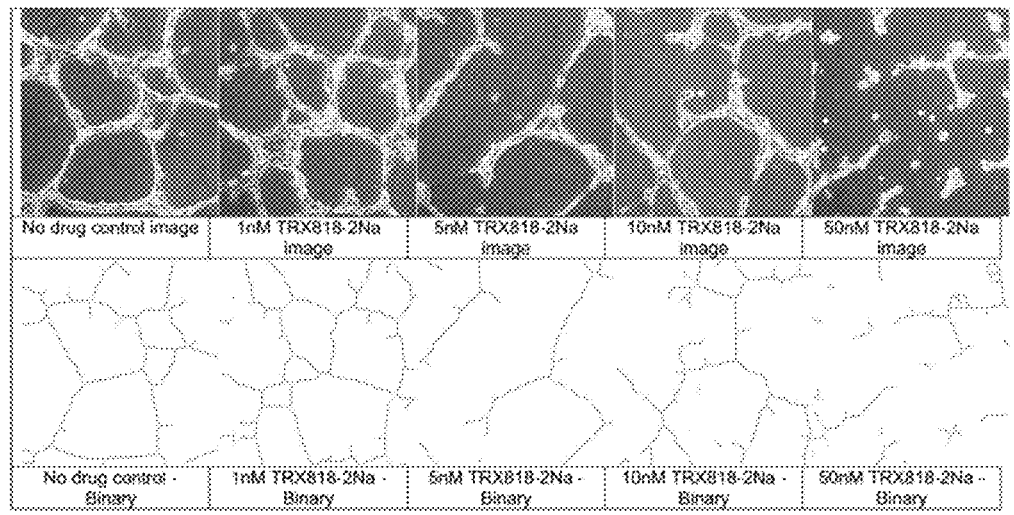
FIG. 3 is a representative binary image illustrating the effect of different concentrations of TRX-818 on the formation of cell junction and tubule length in vehicle group.

VM network formation was inhibited at concentrations ≤5 to 10 nM of TRX-818 in C8161 or SK-MEL28 cancer cells (FIGS. 1 and 2). All tested concentrations of TRX-818 significantly reduced the number of cell junctions and total tubule length formation, which are required for VM formation (FIG. 3). The maximal reduction of cell junctions was achieved by 5 nM (43% reduction) of TRX-818 whereas the maximal reduction of total tubule length was achieved by 50 nM TRX-818 (48% decrease). These results are summarized in Table 5 and suggest that TRX-818 at concentration ≤10 nM inhibits VM network formation by disrupting cell-cell and/or cell-matrix interactions, which may have preceded the anti-proliferative activity of TRX-818 in cancer cells. Table 5 shows the effect of TRX-818 on the number of eel I junctions and total tubule length relative to control. Data are presented as percentage reduction vs. vehicle group.

TABLE 1

| Concentration (nM) | No. of junctions | Total tubule length |
|---|---|---|
| 1 | −16.5% | −15.1% |
| 5 | −43.1% | −23.3% |
| 10 | −35.9% | −26.0% |
| 50 | −42.9% | −47.5% |

Figure 4:
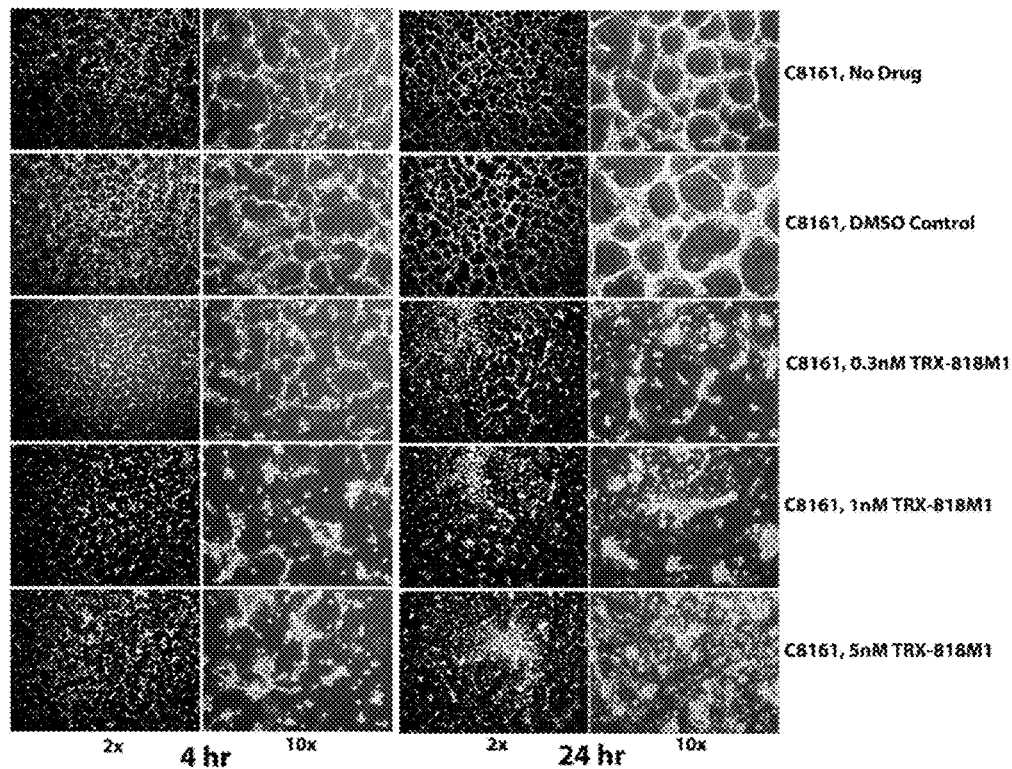
FIG. 4 shows microphotographs Illustrating inhibition of VM network formation by TRX-818M1 in C8161 aggressive melanoma cells.
Figure 5:
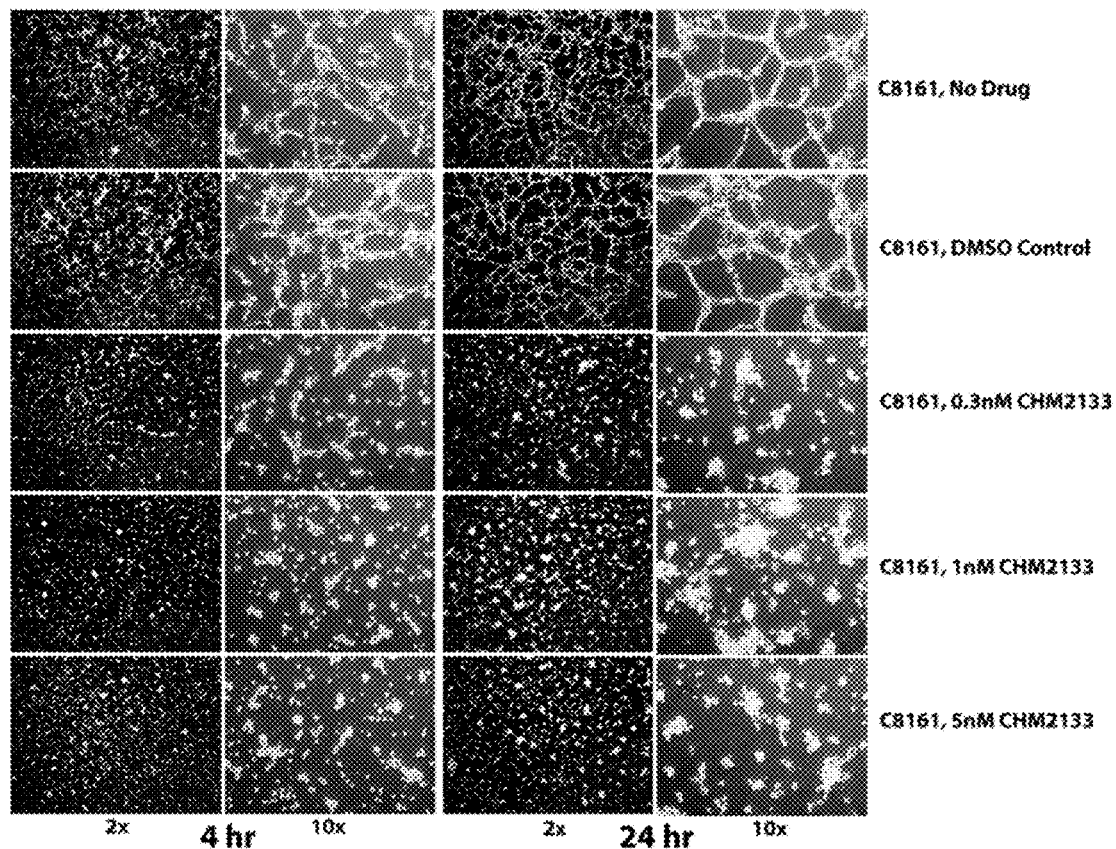
FIG. 5 shows microphotographs illustrating inhibition of VM network formation by CHM2133 in C8161 aggressive melanoma cells.

The similar studies were conducted for the example compounds TRX-818M1 and CHM-2133, The graphic results are shown in FIGS. 4 and 5, respectively.

Example 2

Effect of TRX-818 on the mRNA Levels of VM Proteins

To determine whether TRX-818 reduced the VM network formation by altering the levels of the essential proteins for VM, its effect on Nodal, Notch4, VE-cadherin (CDHE5) or ephrin receptor A2 (Eph A2) expression was determined using qRT-PCR. $2\times10^6$ of aggressive human melanoma (C8161) cells were treated with 10 nM TRX-818 for 8, 24, 48, or 72 h. Sterile deionized water (tissue-culture grade) was used as vehicle.

The mRNA levels of Notch4 intracellular domain (Notch 4 ICD) and Nodal decreased by 75% and 80%, respectively, compared to the control group after 8 hours of treatment. The mRNA levels of Notch4 ICD and Nodal remained at 50% and 70% of the control cells, respectively, after 72 h treatment (FIGS. 6A-D). The mRNA levels of CDH5 decreased by 70% after 8 hours of treatment (10 nM) compared to the control group. The mRNA level of CDH5 remained at 50% of the control cells after 72 hours of continuous exposure to 10 nM TRX-818 (FIGS. 6A-D). These results suggest that TRX-818 reduced the VM network formation by inhibiting the mRNA expression of Notch, Nodal, and CDHE5, but not that of EphA2.

Example 3

Effect of TRX-818 on the Nodal and Smad Protein Levels

To further understand how TRX-818 alters the signaling pathways required for VM network formation, the protein levels of Pro-Nodal, Smad2, and phosphorylated Smad2 (P-Smad2) were determined using immunoblotting analysis. On the day of study, TRX-818 was prepared as described in Example 1, C8161 cells were untreated (control) or treated with 10 nM TRX-818 for 1, 4, 8, and 24 h. Protein expression of Nodal and total Smad2, and P-Smad2 was analyzed by immunoblotting analysis, $5\times10^6$ aggressive human melanoma (C8161) cells were seeded onto a plastic dish in the presence of 10 nM TRX-818, and total proteins were collected for analysis. To quantify the protein levels of Nodal and P-Smad2, 40 µg and 25 µg of total proteins were used for SDS-PAGE and immunoblotting, respectively. The protein level of β-actin was used for normalization to assure equal protein loading.

Figure 7:
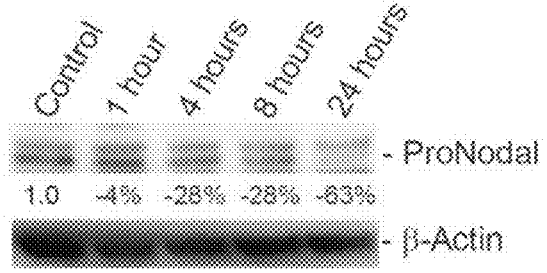
FIG. 7 is a photograph illustrating the effect of TRX-818 on the protein expression of Pro-Nodal.
Figure 8:
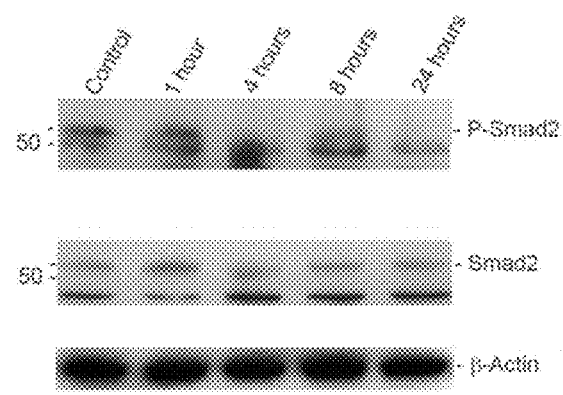
FIG. 8 is a photograph illustrating the effect of TRX-818 on the protein expression and phosphorylated level of Smad.
Figure 6:
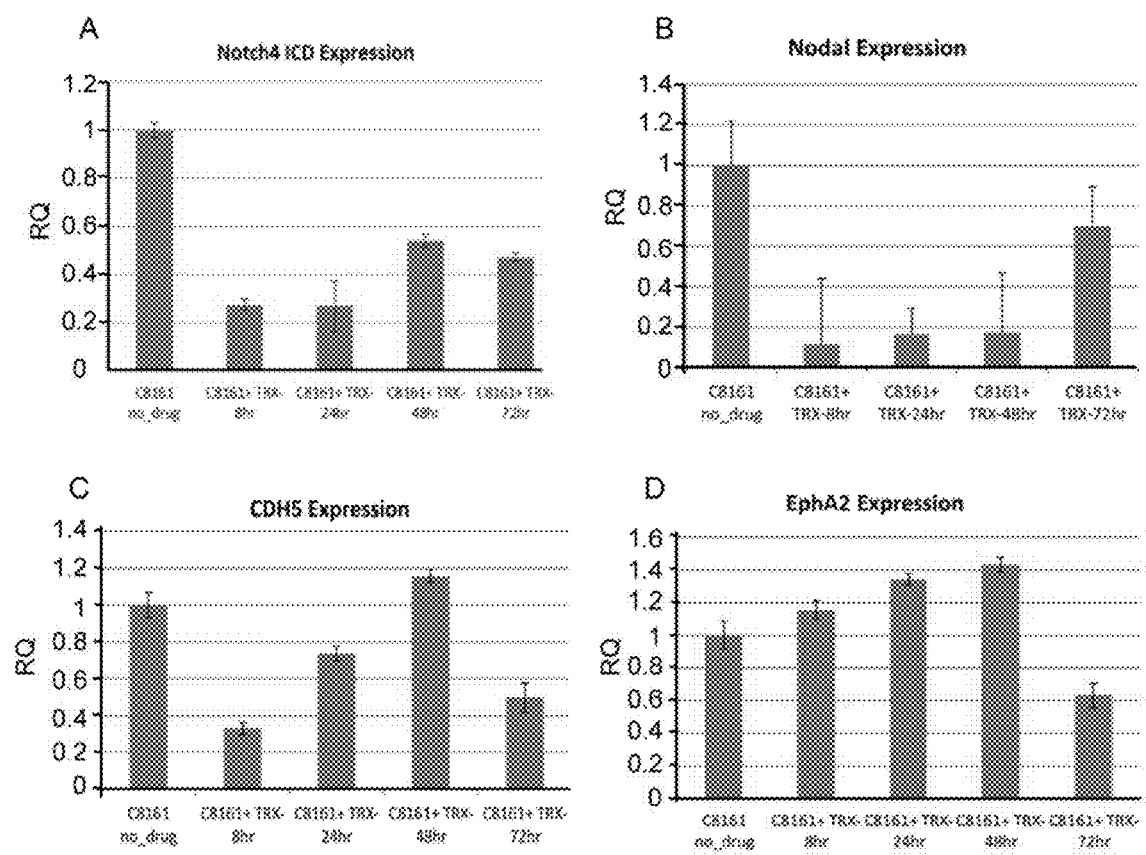
FIGS. 6A-D show the effect of TRX-818 on the expressions of Notch 4 ICD, Nodal, CDH5 and EphA2.

One hour treatment of C8161 cells with 10 nM TRX-818 resulted in a 4% decrease in the Nodal protein expression (detected as Pro-Nodal compared to control cells). Four to eight hours of treatment resulted In a 28% decrease in protein levels, while 24 h treatment resulted in a 63% decrease in the protein level of Pro-Nodal (FIG. 7). Twenty four hours of treatment also reduced the phosphorylation level of Smad-2 (FIG. 8). These results suggest that TRX-818 reduced the VM network formation by decreasing the protein levels of Nodal and phospho-Smad2 in C8161 cells as summarized in Table 2, which shows a summary of the effect of TRX-818 on the Smad protein level and its phosphorylation.

TABLE 2

| | Post-treatment protein level (relative to untreated control cells) | | | |
|---|---|---|---|---|
| | 1 hour | 4 hours | 8 hours | 24 hours |
| P-Smad2/Smad2 | −33% | −60% | −40% | −76% |
| P-Smad2 | −4% | −57% | −39% | −73% |
| Smad2 | +43% | +9% | +3% | +13% |

Taken together, TRX-818 inhibited the VM network formation in aggressive melanoma cells by decreasing the transcriptional, translational expression, and post-translation modification of the essential proteins. First, TRX-818 significantly reduced the mRNA levels of Nodal, Notch4 ICD, and VE-cadherin (CDH5). Second, TRX-818 reduced the protein expression of Pro-Nodal, which is the precursor of Nodal, and the phosphorylation of Smad2. These results suggest that TRX-818 may effectively prevent the upstream to downstream signaling pathways for VM network formation.

Example 4

Effect of TRX-818 in the HCT-116 Orthotopic Human Colon Cancer Xenograft Model

The inhibitory effect of TRX-818 on tumor growth and VM formation of HCT-116, a highly metastatic colon tumor, was examined in a HCT-116 orthotopic xenograft model. The effect of TRX-818 was evaluated on the formation of the vascular or vascular-like (vasculogenic mimicry, VM) network by immunohistochemistry staining (IHC) in orthotopic xenograft human colon cancer model inoculated with HCT116 colon cancer cell lines Six groups were set in this study (ten mice/group). There were: Group 1, TRX-818 at 20 mg/kg given as oral administration; Group 2, TRX-818 at 50 mg/kg given as oral administration; Group 3, TRX-818 at 100 mg/kg given as oral administration; Group 4, TRX-818 at 20 mg/kg given as intravenous injection; Group 5, Irinotecan at 50 mg/kg given as intraperitoneal injection; Group 6, vehicle group. Dose schedule for G1, G2, G3 and G6 was QD×28 and for G4 was QOD×7. Body weights were monitored for safety evaluation. Tumor size and tumor weight were measured at the end of in-life study. The percentage of tumor growth inhibition (TGI %) was calculated at the termination of the study for anti-tumor effect evaluation. The average body weight of study mice on Day 1 was ~20 gram and decreased to ~17-19 gram at the end of study (Day 42)

At the end of 28-day dosing, $CO_2$ anesthesia (1 min) followed by cervical dislocation was used for mice euthanasia in the study prior to tumors and lungs excision. First, a ventral midline incision was made and colon with primary tumor was excised and collected. The tumor collection was completed in 3 minutes after euthanasia. The tissues were rinsed with PBS to remove the blood before fixation.

The number of channels with $CD31^+$/red blood cell $(RBC)^+$ or $CD31^-/RBC^+$ were counted on the whole section of each sample in each group, and the number of vessels with CD31 positive or negative staining were counted based on 5 light fields (200×) under microscope. The vascular network represented by the $CD31^+/RBC^+$ staining whereas the VM network represented by $CD31^-/RBC^+$ staining, because the VM formation is independent of vascular endothelial cells. The scoring was conducted by blinded, objective observer.

Figure 9:
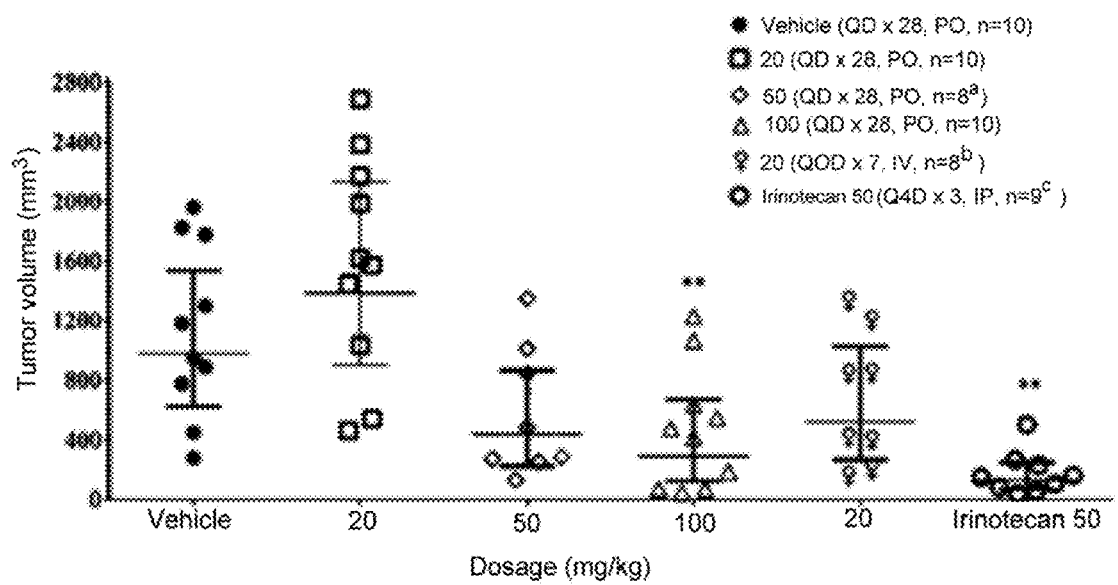
FIG. 9 shows the effect of TRX-818 on tumor volume in HCT-116 colon cancer orthotopic xenograft model on Day 43 post tumor inoculation. a: In the 50 mg/kg QD group one animal was found dead prior to study termination and one data point was outlier detected by β-distribution outlier analysis. b: In the 20 mg/kg QOD group two animals were found dead prior to study termination. c: In the Irinotecan 50 Q4D group one data point was outlier detected by β-distribution outlier analysis. *p<0.05 vs. vehicle, **p<0.01 vs. vehicle.

In the HCT-116 orthotopic human colon cancer xenograft model (Ortho), TRX-818 at 50 mg/kg significantly reduced tumor volume by 49%, compared to the vehicle group (FIG. 9). The MED for orally administered TRX-818 was 50 mg/kg.

Figure 10:
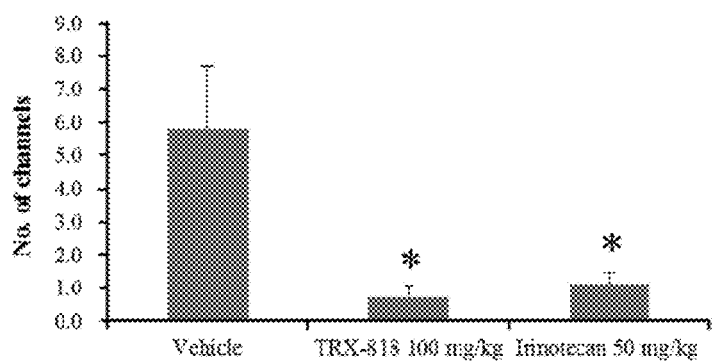
FIG. 10 shows the effect of TRX-818 on the number of VM channels in HCT-116 colon cancer orthotopic xenograft model. *P<0.05 vs. vehicle group.

The average number of channels with $CD31^-/RBC^+$ in both Groups (TRX-818 100 mg/kg QD×28, p.o.) and Group 5 (Irinotecan 50 mg/kg Q4D×3, i.p.) was significantly decreased compared with that in the vehicle group (FIG. 10). $CD31^-$ representing the formation of vasculogenic mimicry (VM) formation. These results suggested that compound TRX-818 as a single agent demonstrated beneficial effect on inhibiting the HCT116 tumor cells to form the vasculogenic mimicry structure. Table 3 shows the number of VM Channels ($CD31^-/RBC^+$) in the Orthotopic HCT116 Human Colon Cancer Xenograft Model.

TABLE 3

| Groups | Treatment | Average number of channels in the whole tumor section per group[a] | P Value[b] |
|---|---|---|---|
| 6 | Vehicle | 5.8 ± 1.9 | — |
| 3 | TRX-818 100 mg/kg QD×28, p.o. | 0.8 ± 0.3 | 0.006* |
| 5 | Irinotecan 50 mg/kg Q4D×3, i.p. | 1.1 ± 0.4 | 0.010* |

Note:
[a]Mean ± SEM;
[b]vs. vehicle control. P-value is from 2-tailed Mann-Whitney U test, uncorrected from multiple comparisons.

Example 5

TRX-818M1 Inhibits Vasculogenic Mimicry Network Formation in Aggressive Melanoma Cells

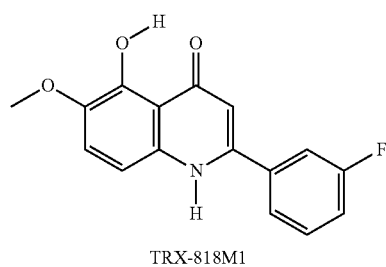

TRX-818M1

Solutions of TRX-818M1 (2-(3-fluorophenyl)-6-methoxy-4-oxo-1,4-dihydroquinolin-5-yl) were prepared in a similar manner as in Example 1 except that TRX-818M1 was used to replace the TRX-818 in sodium salt form.

Aggressive human melanoma (C8161, $7.5×10^4$) cells were seeded as disclosed in Example 1. C8161 cells were treated tor 4 h or 24 h with 0.3, 1 or 5 nM of TRX-818M1. Another set of melanoma cells were seeded onto a plastic dish and treated for the same amount of time before the cell viability of C8161 cells was determined.

VM network formation was inhibited in C8161 cancer cells at all tested concentrations of TRX-818M1 (FIG. 4). TRX-818M1 appears to be a potent vascular disrupting agent effective at picomolar concentrations (~0.3 nM). Higher concentrations in the nM range induced cell death.

Example 6

CHM-2133 Inhibits Vasculogenic Mimicry Network Formation in Aggressive Melanoma Cells

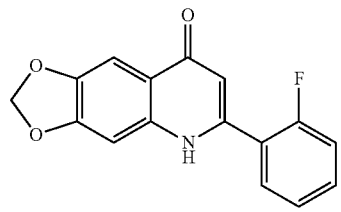

CHM-2133

Solutions of CHM-2133 (2-(2-fluorphenyl)-6,7-methylenedioxyquinolin-4-one) were prepared in a similar manner as in Examples 1 and 5. VM network formation was inhibited in C8161 cancer cells at all tested concentrations of CHM-2133 (FIG. 5). CHM-2133 appears to be a potent vascular disrupting agent effective at picomolar concentrations (~0.3 nM), Example 7

Inhibition of Vasculogenic Mimicry Network Formation in Aggressive Melanoma Cells Compounds 16-24, 37-45, 48-53, 124-143, 143a, 143b, 144, 144a, 144b, 146-147, 152-153, 157-158, 166-169 shown in Table 4 were synthesized according to the method disclosed in U.S. Pat. No. 8,524,740. Their effects on inhibition of vasculogenic mimicry network formation in aggressive melanoma cells are tested using the method as described in Example 1.

Example 8

Effect on the mRNA Levels of VM Proteins

Compounds shown in Table 4 are examined for their effects on the mRNA levels of VM proteins using the method as described in Example 2.

Example 9

Effect on the Nodal and Smad Protein Levels

Compounds shown in Table 4 are examined for their effects on the Nodal and Smad protein levels using the method as described in Example 3.

Example 10

Effect of Quinolin Derivatives in the HCT-116 Orthotopic Human Colon Cancer Xenograft Model Compounds shown in Table 4 are examined for their effects using the HCT-116 orthotopic human colon cancer xenograft model as described in Example 4.

Example 11

Effect of TRX-818 Structurally Similar Compounds on Inhibition of Vasculogenic Mimicry TRX-818 M1 (i.e., compound No. 38) structurally similar compounds were tested for their effect on inhibition of vasculogenic mimicry. Aggressive human melanoma (SK-MEL-28 from ATCC®; $7.5 \times 10^4$ mL medium) cells were seeded onto a three-dimensional polymerized MATRIGEL™-coated 24-well plate. After 18 h of cell seeding, VM network was formed. The medium was then replaced with negative controls (untreated and DMSO treated controls), a positive control (100 nM of TRX-818M1) or 100 nM of each testing compound. The VM network formation was observed at 0 h, 5 h, and 24 h post treatment.

Figure 11:
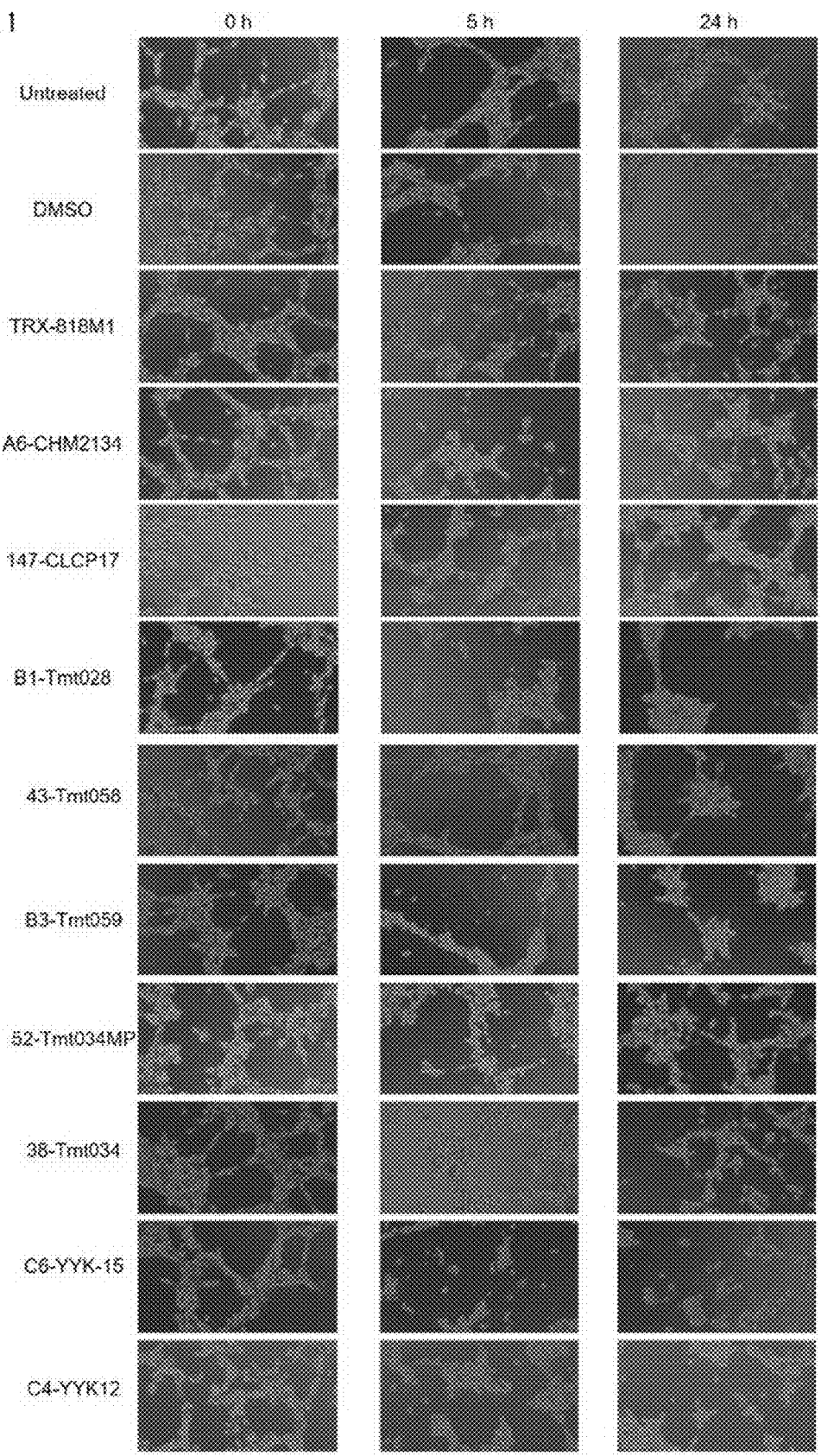
FIG. 11 shows microphotographs illustrating the effect of TRX-818 structurally similar compounds on VM network formation in aggressive melanoma cells.

It was found that TRX-818 structurally similar compounds showed an inhibitory effect on VM network formation. SK-MEL28 cells (human, melanoma cell line) treated with compounds TRX-818M1 (the positive control, epd. 38), 43, 52, 147, A6, B1, B3, C4 and C6 at 100 nM show a mild loss of VM network at 5 h post treatment as compared to the negative controls (untreated and DMSO treated controls), and a marked loss of VM network at 24 h post treatment (FIG. 11). It is noted that while a concentration at 100 nM of the testing compounds is inhibitory to VM network formation, it is mildly cytotoxic to SR-MEL-28 cells.

TABLE 4

Formula X

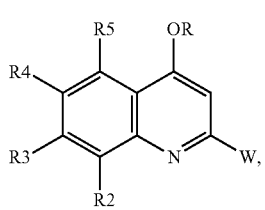

Formula X wherein W = is an aromatic group selected from the group consisting of subtituted benzene (Formula Ia or Ib), naphthyl, quinolin benzofuranyl, benzothiophene, or anthracene;

TABLE 4-continued

Formula Ia ↔ Formula Ib

| Comp'd | Structure | Name | Substituent on Formula 1 |
|---|---|---|---|
| 16 | 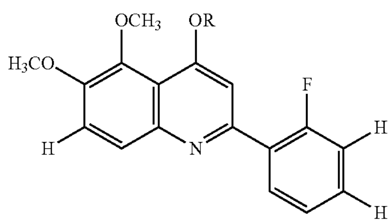 | 2-(2-Fluorophenyl)-5,6-dimethoxyquinolin-4-one | R, $R_5'$, $R_4'$, $R_3'$, $R_2'$ = H<br>$R_6'$ = fluoro<br>$R_5$ = methoxy<br>$R_4$ = methoxy<br>$R_3$, $R_2$ = H |
| 17 | 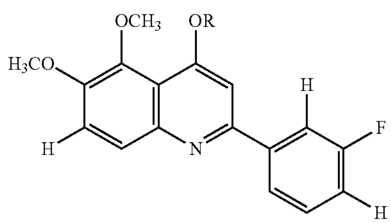 | 2-(3-Fluorophenyl)-5,6-dimethoxyquinolin-4-one | R, $R_6'$, $R_4'$, $R_3'$, $R_2'$ = H<br>$R_5'$ = fluoro<br>$R_5$ = methoxy<br>$R_4$ = methoxy<br>$R_3$, $R_2$ = H |
| 18 | 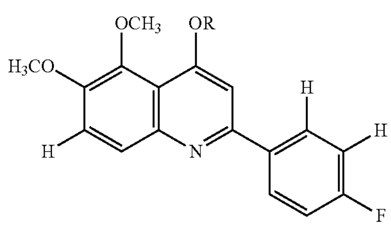 | 2-(4-Fluorophenyl)-5,6-dimethoxyquinolin-4-one | R, $R_6'$, $R_5'$ $R_3'$, $R_2'$ = H<br>$R_4'$ = fluoro<br>$R_5$ = methoxy<br>$R_4$ = methoxy<br>$R_2$, $R_3$ = H |
| 19 | 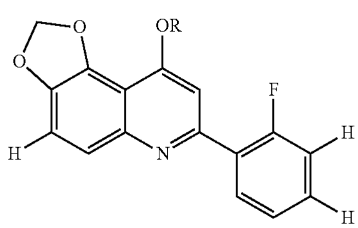 | 2-(2-Fluorophenyl)-5,6-methylenedioxyquinolin-4-one | R, $R_5'R_4'R_3'R_2'$ = H<br>$R_6'$ = fluoro<br>$R_4$, $R_5$ = methylenedioxy<br>$R_2$, $R_3$ = H |
| 20 | 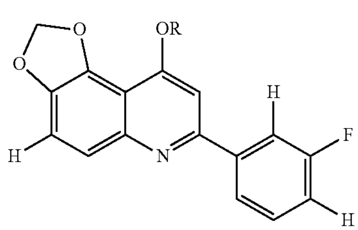 | 2-(3-Fluorophenyl)-5,6-methylenedioxyquinolin-4-one | R, $R_6'$, $R_4'$, $R_3'$, $R_2'$ = H<br>$R_5'$ = fluorol<br>$R_4$, $R_5$ = methylenedioxy<br>$R_2$, $R_3$ = H |

TABLE 4-continued

| | | | |
|---|---|---|---|
| 21 | 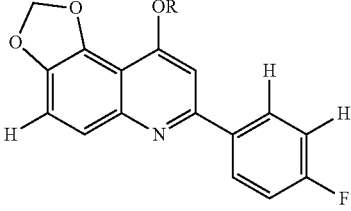 | 2-(4-Fluorophenyl)-5,6-methylene-dioxyquinolin-4-one | R, R$_6$', R$_5$', R$_3$', R$_2$' = H<br>R$_4$' = Fluoro<br>R$_4$, R$_5$ = methylenedioxy<br>R$_2$, R$_3$ = H |
| 22 | 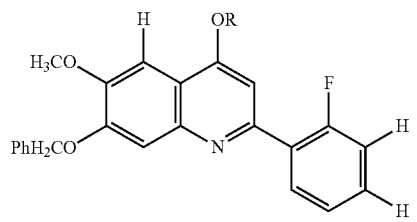 | 7-Benzyloxy-2-(2-fluorophenyl)-6-methoxyquinolin-4-one | R, R$_5$', R$_4$', R$_3$', R$_2$' = H<br>R$_6$' = fluoro<br>R$_5$, R$_2$ = H<br>R$_4$ = methoxy<br>R$_3$ = O-benzyl |
| 23 | 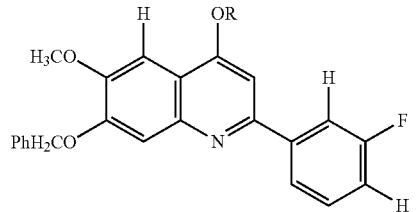 | 7-Benzyloxy-2-(3-fluorophenyl)-6-methoxyquinolin-4-one | R, R$_6$', R$_4$', R$_3$', R$_2$' = H<br>R$_5$' = fluoro<br>R$_5$, R$_2$ = H<br>R$_4$ = methoxy<br>R$_3$ = O-benzyl |
| 24 | 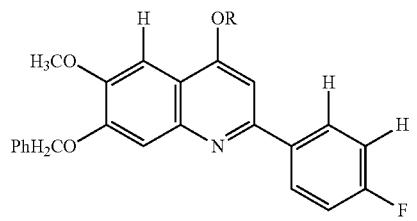 | 7-Benzyloxy-2-(4-fluorophenyl)-6-methoxyquinolin-4-one | R, R$_6$', R$_5$', R$_3$', R$_2$' = H<br>R$_4$' = fluoro<br>R$_5$, R$_2$ = H<br>R$_4$ = methoxy<br>R$_3$ = O-benzyl |
| 37 | 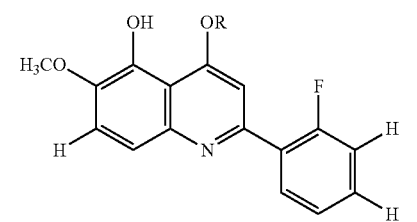 | 2-(2-Fluorophenyl)-5-hydroxy-6-methoxyquinolin-4-one | R, R$_5$', R$_4$', R$_3$', R$_2$' = H<br>R$_6$' = fluoro<br>R$_5$ = hydroxyl<br>R$_4$ = methoxy<br>R$_3$, R$_2$ = hydrogen |
| 38 | 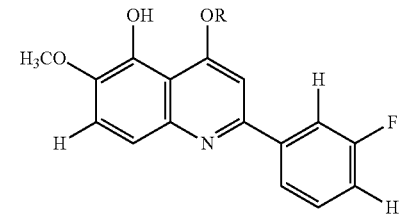 | 2-(3-Fluorophenyl)-5-hydroxy-6-methoxyquinolin-4-one | R, R$_6$', R$_4$', R$_3$', R$_2$' = H<br>R$_5$' = fluoro<br>R$_5$ = hydroxyl<br>R$_4$ = methoxy<br>R$_3$, R$_2$ = hydrogen |
| 39 | 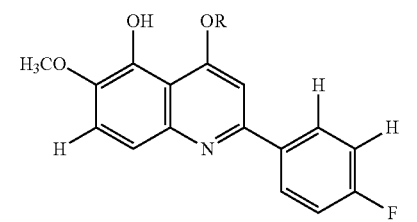 | 2-(4-Fluorophenyl)-5-hydroxy-6-methoxyquinolin-4-one | R, R$_6$', R$_5$', R$_3$', R$_2$' = H<br>R$_4$' = fluoro<br>R5 = hydroxyl<br>R$_4$ = methoxy<br>R$_3$, R$_2$ = hydrogen |

TABLE 4-continued

| | | | |
|---|---|---|---|
| 40 | 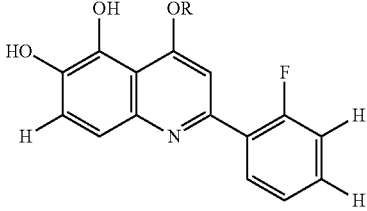 | 2-(2-Fluorophenyl)-5,6-dihydroxyquinolin-4-one | R, R$_5$', R$_4$', R$_3$', R$_2$' = H<br>R$_6$'= fluorol<br>R$_5$, R$_4$ = hydroxyl<br>R$_3$, R$_2$ = H |
| 41 | 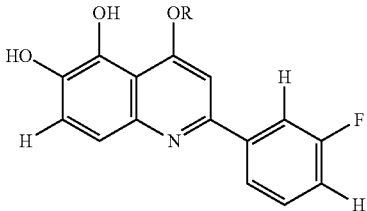 | 2-(3-Fluorophenyl)-5,6-dihydroxyquinolin-4-one | R, R$_6$', R$_4$', R$_3$', R$_2$' = H<br>R$_5$' = fluoro<br>R$_5$ = hydroxyl<br>R$_4$ = hydroxyl<br>R$_3$, R$_2$ = hydrogen |
| 42 | 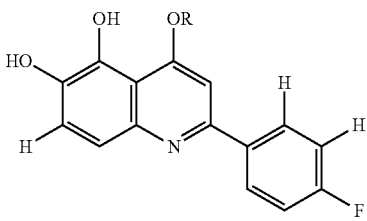 | 2-(4-Fluorophenyl)-5,6-dihydroxyquinolin-4-one | R, R$_6$', R$_5$', R$_3$', R$_2$' = H<br>R$_4$' = fluoro<br>R$_5$, R$_4$ = hydroxyl<br>R$_3$, R$_2$ = hydrogen |
| 43 | 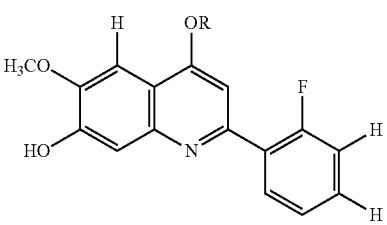 | 2-(2-Fluorophenyl)-7-hydroxy-6-methoxyquinolin-4-one | R, R$_5$', R$_4$', R$_3$', R$_2$' = H<br>R$_6$' = fluoro<br>R$_5$, R$_2$ = H<br>R$_4$ = methoxy<br>R$_3$ = hydroxyl |
| 44 | 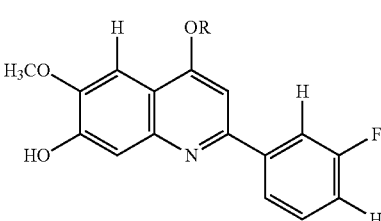 | 2-(3-Fluorophenyl)-7-hydroxy-6-methoxyquinolin-4-one | R, R$_6$', R$_4$', R$_3$', R$_2$' = H<br>R$_5$' = fluoro<br>R$_5$, R$_2$ = hydrogen<br>R$_4$ = methoxy<br>R$_3$ = hydroxyl |
| 45 | 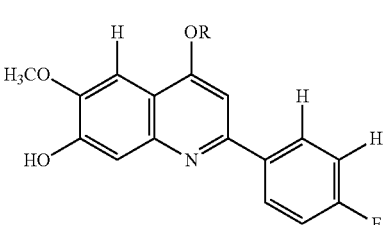 | 2-(4-Fluorophenyl)-7-hydroxy-6-methoxyquinolin-4-one | R, R$_6$', R$_5$', R$_3$', R$_2$' = H<br>R$_4$' = fluoro<br>R, R$_2$ = H<br>R$_4$ = methoxy<br>R$_3$ = hydroxyl |
| 48 | 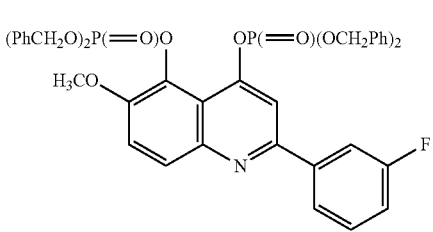 | 2-(3-Fluorophenyl)-6-methoxyquinoline-4,5-diyl bis(dibenzyl phosphate) | R = P = O(O-benzyl)$_2$<br>R$_5$' = fluoro<br>R$_5$ = OP(=O)(O-benzyl)$_2$<br>R$_4$ = methoxy<br>R$_6$', R$_4$', R$_3$', R$_2$',<br>R$_3$, R$_2$ = H |

TABLE 4-continued

| # | Structure | Name | Substituents |
|---|---|---|---|
| 49 | (HO)₂P(=O)O / OP(=O)(OH)₂ on H₃CO-quinoline-2-(3-fluorophenyl) | 2-(3-Fluorophenyl)-6-methoxyquinoline-4,5-diyl bis(dihydrogen phosphate) | R = PO(OH)2<br>$R_5'$ = fluoro<br>$R_6'$, $R_4'$, $R_3'$, $R_2'$ = H<br>$R_4$ = methoxy<br>$R_3$, $R_2$ = hydrogen<br>$R_5$ = —OP(=O)(OH)₂ |
| 50 | (NaO)₂P(=O)O / OP(=O)(ONa)₂ on H₃CO-quinoline-2-(3-fluorophenyl) | 2-(3-Fluorophenyl)-6-methoxyquinoline-4,5-diyl bis(disodium phosphate) | R = PO(ONa)2<br>$R_5'$ = fluoro<br>$R_6'$, $R_4'$, $R_3'$, $R_2'$ = H<br>$R_4$ = methoxy<br>$R_3$, $R_2$ = hydrogen<br>$R_5$ = OP(=O)(ONa)₂ |
| 51 | (PhCH₂O)₂P(=O)O / OH on H₃CO-quinoline-2-(3-fluorophenyl) | Dibenzyl 2-(3-fluorophenyl)-6-methoxy-4-oxo-1,4-dihydroquinolin-5-yl phosphate | R, $R_3$, $R_2$, $R_6'$, $R_4'$, $R_3'$, $R_2'$ = H<br>$R_5'$ = fluoro<br>R5 = OP(=O)(O-benzyl)₂<br>$R_4$ = methoxy |
| 52 | (HO)₂P(=O)O / OH on H₃CO-quinoline-2-(3-fluorophenyl) | 2-(3-Fluorophenyl)-6-methoxy-4-oxo-1,4-dihydroquinolin-5-yl dihydrogen phosphate | R, $R_6'$, $R_4'$, $R_3'$, $R_2'$, $R_3$, $R_2$ = H<br>$R_5$ = fluoro<br>$R_5$ = OP(=O)(OH)2<br>$R_4$ = methoxy |
| 53 | (NaO)₂P(=O)O / OR on H₃CO-quinoline-2-(3-fluorophenyl) | Sodium 2-(3-fluorophenyl)-6-methoxy-4-oxo-1,4-dihydroquinolin-5-yl phosphate | R, $R_6'$, $R_4'$, $R_3'$, $R^{2'}$ = H<br>$R_5'$ = fluoro<br>$R_5$ = OP(=O)(ONa)2<br>$R_4$ = methoxy<br>$R_3$, $R_2$ = H |
| 124 | morpholino-quinoline with OR, 2-(benzo[d][1,3]dioxol-4-yl) | 2-(benzo[d][1,3]dioxol-23-yl)-6-morpholinoquinolin-4-one | R, $R_4$, $R_3'$, $R_2'$ = H<br>$R_6'$, $R_5'$ = methylenedioxy<br>$R_5$ = H<br>$R_4$ = N-morpholino<br>$R_3$, $R_2$ = H |
| 125 | pyrrolidino-quinoline with OR, 2-(benzo[d][1,3]dioxol-4-yl) | 2-(benzo[d][1,3]dioxol-4-yl)-6-pyrrolidinoquinolin-4-one | R, $R_3'$, $R_2'$ = H<br>$R_6'$, $R_5'$ = methylenedioxy<br>$R_3$, $R_2$ = H<br>$R_4$ = N-pyrrolindino |

TABLE 4-continued

| | | | |
|---|---|---|---|
| 126 | 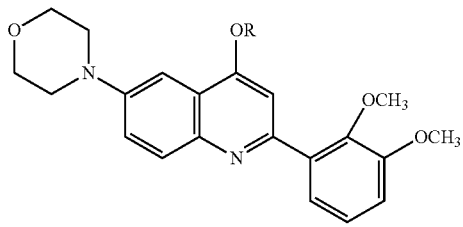 | 2-(2,3-dimethoxyphenyl)-6-morpholinoquinolin-4-one | R, R$_3$', R$_2$' = H<br>R$_6$', R$_5$' = methoxyl<br>R$_5$, R$_3$, R$_2$ = H<br>R$_4$ = N-morpholino |
| 127 | 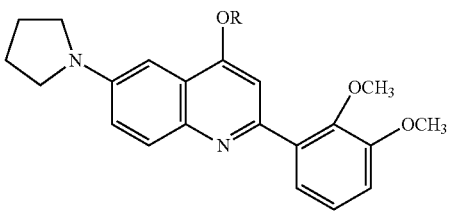 | 2-(2,3-dimethoxyphenyl)-6-pyrrolidinoquinolin-4-one | R, R$_3$', R$_2$' = H<br>R$_6$', R$_5$' = methoxy<br>R$_5$, R$_3$, R$_2$ = H<br>R$_4$ = N-pyrrolindino |
| 128 | 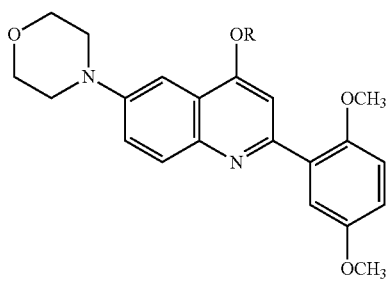 | 2-(2,5-dimethoxyphenyl)-6-morpholinoquinolin-4-one | R, R$_5$', R$_4$', R$_2$' = H<br>R$_6$', R$_3$' = methoxy<br>R$_5$, R$_3$, R$_2$ = H<br>R$_4$ = N-morpholino |
| 129 | 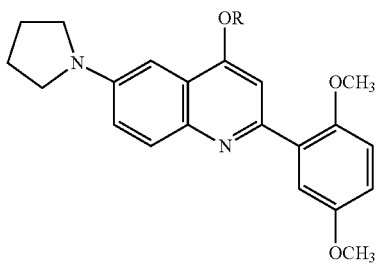 | 2-(2,5-dimethoxyphenyl)-6-pyrrolidinoquinolin-4-one | R, R$_5$', R$_4$', R$_2$ = H<br>R$_6$', R$_3$' = methoxyl<br>R$_5$, R$_3$, R$_2$ = H<br>R$_4$ = N-pyrrolindino |
| 130 | 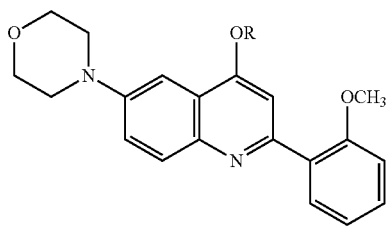 | 2-(2-methoxyphenyl)-6-morpholinoquinolin-4-one | R, R$_5$', R$_4$', R$_3$', R$_2$' = H<br>R$_6$' = methoxyl<br>R$_5$, R$_3$, R$_2$ = H<br>R$_4$ = N-morpholino |
| 131 | 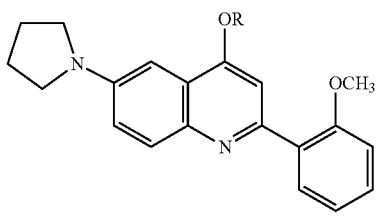 | 2-(2,5-dimethoxyphenyl)-6-pyrrolidinoquinolin-4-one | R, R$_5$', R$_4$', R$_3$', R$_2$' = H<br>R$_6$' = methoxy<br>R$_5$, R$_3$, R$_2$ = H<br>R$_4$ = N-pyrrolindino |

TABLE 4-continued

| | | | |
|---|---|---|---|
| 132 | 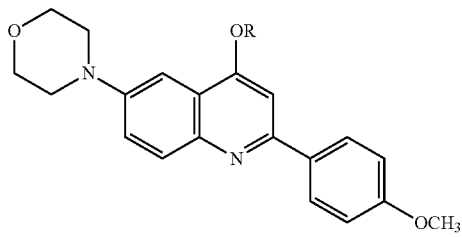 | 2-(4-methoxyphenyl)-6-morpholinoquinolin-4-one | R, R6', R5', R3', R2' = H<br>R4' = methoxy<br>R5, R3, R2 = H<br>R4 = N-morpholino |
| 133 | 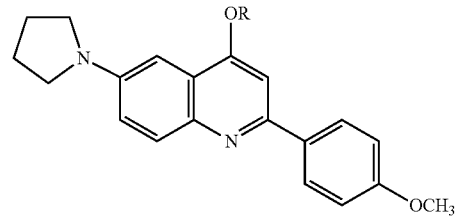 | 2-(4-methoxyphenyl)-6-pyrrolidinoquinolin-4-one | R, R6', R5', R3', R2' = H<br>R4' = methoxy<br>R5, R3, R2 = H<br>R4 = N-pyrrolindino |
| 134 | 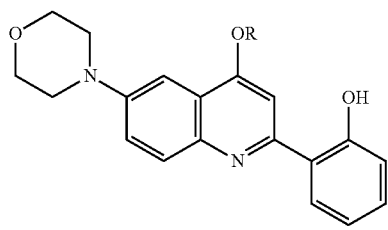 | 2-(2-Hydroxyphenyl)-6-morpholinoquinolin-4-one | R, R5', R4', R3', R2' = H<br>R6' = hydroxy<br>R5, R3, R2 = H<br>R4 = N-morpholino |
| 135 | 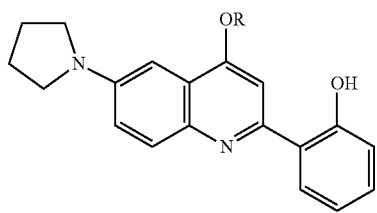 | 2-(2-hydroxyphenyl)-6-pyrrolidinoquinolin-4-one | R, R5', R4', R3', R2' = H<br>R6' = hydroxy<br>R5, R3, R2 = H<br>R4 = N-pyrrolindino |
| 136 | 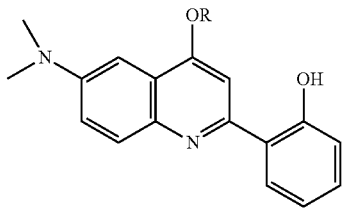 | 2-(2-hydroxyphenyl)-6-dimethylamino-quinolin-4-one | R, R5', R4', R3', R2' = H<br>R6' = hydroxy<br>R5, R3, R2 = H<br>R4 = N,N-dimethylamino |
| 137 | 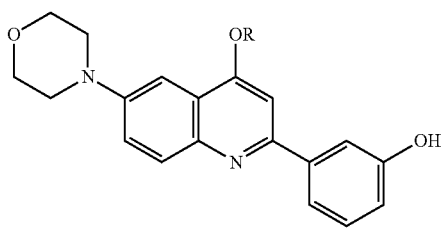 | 2-(3-Hydroxyphenyl)-6-morpholinoquinolin-4-one | R, R6', R4', R3', R2', = H<br>R5' = hydroxy<br>R5, R3, R2 = H<br>R4 = N-morpholino |
| 138 | 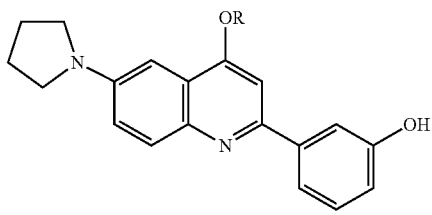 | 2-(3-hydroxyphenyl)-6-pyrrolidinoquinolin-4-one | R, R6', R4', R3', R2' = H<br>R5' = hydroxy<br>R5, R3, R2 = H<br>R4 = N-pyrrolindino |

TABLE 4-continued

| 139 | 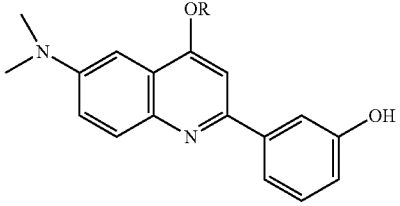 | 2-(3-hydroxyphenyl)-6-dimethylamino-quinolin-4-one | R, R$_6$'R$_4$'R$_3$', R$_2$' = H<br>R$_5$' = hydroxy<br>R$_5$, R$_3$, R$_2$ = H<br>R$_4$ = N,N-dimethylamino |
| --- | --- | --- | --- |
| 140 | 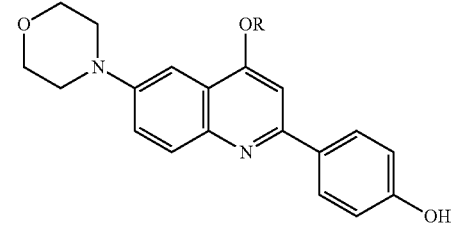 | 2-(4-Hydroxyphenyl)-6-morpholinoquinolin-4-one | R, R$_6$', R$_5$', R$_3$', R$_2$' = H<br>R$_4$' = hydroxy<br>R$_5$, R$_3$, R$_2$ = H<br>R$_4$ = N-morpholino |
| 141 | 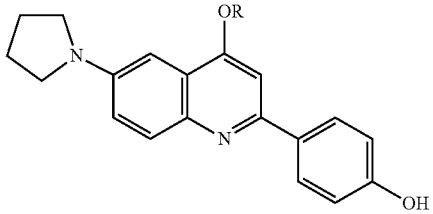 | 2-(4-hydroxyphenyl)-6-pyrrolidinoquinolin-4-one | R, R$_6$', R$_5$', R$_3$', R$_2$' = H<br>R$_4$' = hydroxy<br>R$_5$, R$_3$, R$_2$ = H<br>R$_4$ = N-pyrrolindino |
| 142 | 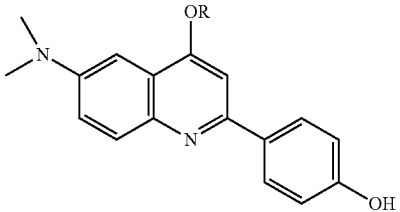 | 2-(4-hydroxyphenyl)-6-dimethylamino-quinolin-4-one | R, R$_6$', R$_5$', R$_3$', R$_2$' = H<br>R$_4$' = hydroxy<br>R$_5$, R$_3$, R$_2$ = H<br>R$_4$ = N,N-dimethylamino |
| 143 | 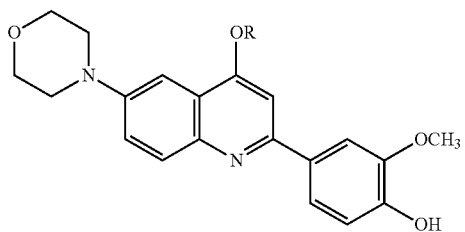 | 2-(4-hydroxy-3-methoxyphenyl)-6-morpholinoquinolin-4-one | R, R$_6$', R$_3$', R$_2$' = H<br>R$_5$' = methoxy<br>R$_4$' = hydroxy<br>R$_4$ = N-morpholino<br>R$_5$, R$_3$, R$_2$ = H |
| 143a | 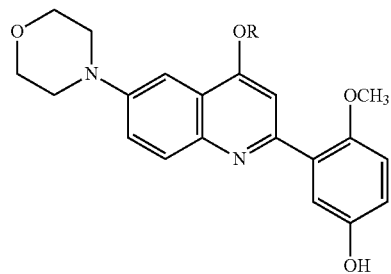 | 2-(5-hydroxy-2-methoxyphenyl)-6-morpholinoquinolin-4-one | R, R$_5$', R$_4$', R$_2$' = H<br>R$_6$' = -methoxy<br>R$_3$' = hydroxy<br>R$_4$ = N-morpholino<br>R$_5$, R$_3$, R$_2$ = H |

TABLE 4-continued

| | | | |
|---|---|---|---|
| 143b | 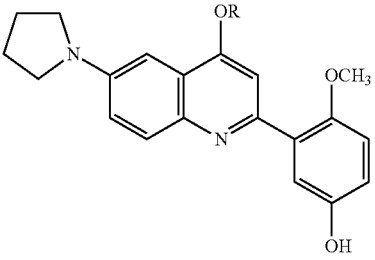 | 2-(5-hydroxy-2-methoxphenyl)--6-pyrrolidinoquinolin-4-one | R, R$_5$', R$_4$', R$_2$' = H<br>R$_6$' = methoxphenyl<br>R$_3$' = hydroxy<br>R$_4$ = N-pyrrolindino<br>R$_5$, R$_3$, R$_2$ = H |
| 144 | 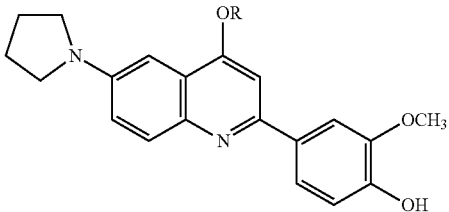 | 2-(4-hydroxy-3-methoxyphenyl)-6-pyrrolidinoquinolin-4-one | R, R$_6$', R$_3$', R$_2$' = H<br>R$_5$' = methoxy<br>R$_4$' = hydroxy<br>R$_4$ = N-pyrrolindino<br>R$_5$, R$_3$, R$_2$ = H |
| 144a | 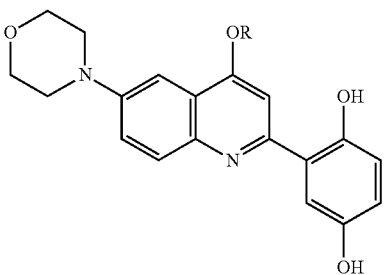 | 2-(2,5-dihydroxy-phenyl)-6-morpholinoquinolin-4-one | R, R$_5$', R$_4$', R$_2$' = H<br>R$_6$', R$_3$' = hydroxy<br>R$_5$, R$_3$, R$_2$ = H<br>R$_4$ = N-morpholino |
| 144b | 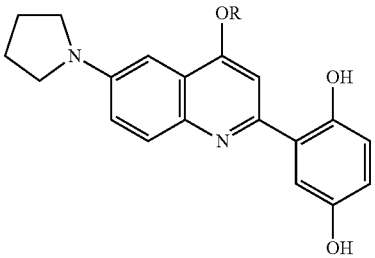 | 2-(2,5-dihydroxy-phenyl)--6-pyrrolidinoquinolin-4-one | R, R$_5$', R$_4$', R$_2$' = H<br>R$_6$', R$_3$' = hydroxy<br>R5, R$_3$, R$_2$ = H<br>R$_4$ = N-pyrrolindino |
| 146 | 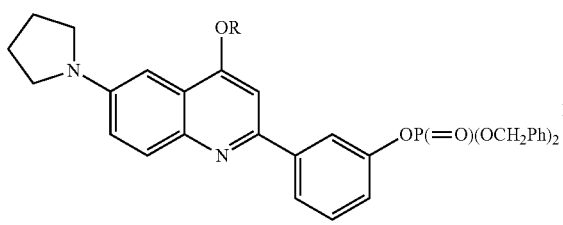 | Dibenzyl 3-(4-oxo-6-(pyrrolidin-1-yl)-1,4-dihydroquinolin-2-yl)phenyl phosphate | R, R$_6$', R$_4$', R$_3$', R$_2$' = H<br>R$_5$' = OP(=O)(O-benzyl)$_2$I<br>R$_5$, R$_3$, R$_2$ = H<br>R$_4$ = N-pyrrolindino |
| 147 | 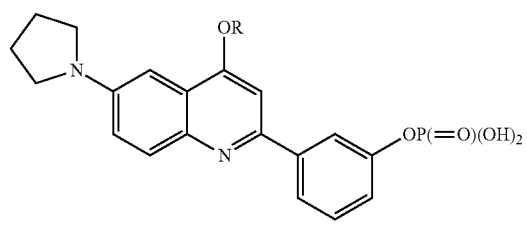 | 3-(4-Oxo-6-(pyrrolidin-1-yl)-1,4-dihydroquinolin-2-yl)phenyl dihydrogen phosphate | R, R$_6$', R$_4$', R$_3$', R$_2$' = H<br>R$_5$' = OP(=O)(OH)$_2$<br>R$_5$, R$_3$, R$_2$ = H<br>R$_4$ = N-pyrrolindino |

TABLE 4-continued

| # | Structure | Name | Substituents |
|---|---|---|---|
| 151 (JMC-39) | [structure: 4-OR, 6,7-methylenedioxy, 2-(naphth-1-yl)quinoline] | 2-(1-Naphthalenyl)-6,7-methylene-dioxyquinolin-4-one | R = H<br>W = naphtha-1-yl<br>R5, R2 = hydrogen<br>R4, R3 = methylenedioxy |
| 152 | [structure: 4-OP(=O)(OCH2Ph)2, 6,7-methylenedioxy, 2-(naphth-1-yl)quinoline] | Dibenzyl 2-(1-naphthalenyl)-6,7-methylenedioxy-quinolin-4-yl phosphate | R = P(=O)(O-benzyl)2<br>W = naphtha-1-yl<br>R5, R2 = H<br>R4 and R3 = methylenedioxy |
| 153 | [structure: 4-OP(=O)(OH)2, 6,7-methylenedioxy, 2-(naphth-1-yl)quinoline] | 2-(1-Naphthalenyl)-6,7-methylenedioxy-quinolin-4-yl dihydrogen phosphate | R = P(=O)(OH)2<br>W = naphtha-1-yl<br>R5, R2 = H<br>R4 and R3 = methylenedioxy |
| 156 (JMC-37) | [structure: 4-OR, 6,7-methylenedioxy, 2-(benzo[b]furan-3-yl)quinoline] | 2-(3-Benzo[b]furyl)-6,7-methylenedioxy-quinolin-4-one | R, R5, R2 = H<br>W = benzo[b]furan-3-yl<br>R4 and R3 = methylenedioxy |
| 157 | [structure: 4-OP(=O)(OCH2Ph)2, 6,7-methylenedioxy, 2-(benzo[b]furan-3-yl)quinoline] | Dibenzyl 2-(3-benzo[b]furyl)-6,7-methylenedioxy-quinolin-4-yl phosphate | R = P(=O)(O-benzyl)2<br>W = benzo[b]furan-3-yl<br>R5, R2 = H<br>R4 and R3 = methylenedioxy |
| 158 | [structure: 4-OP(=O)(OH)2, 6,7-methylenedioxy, 2-(benzo[b]furan-3-yl)quinoline] | 2-(3-Benzo[b]furyl)-6,7-methylenedioxy-quinolin-4-yl dihydrogen phosphate | R = P(=O)(OH)2<br>W = benzo[b]furan-3-yl<br>R5, R2 = H<br>R4 and R3 = methylenedioxy |
| 166 | [structure: 4-OR, 6,7-methylenedioxy, 2-(3-hydroxy-5-methoxyphenyl)quinoline] | 2-(3-Hydroxy-5-methoxyphenyl)-6,7-methylene-dioxyquinolin-4-one | R, R6', R4', R2' = H<br>R5' = -methoxyl<br>R3' = hydroxyl<br>R5, R2 = H<br>R4 and R3 = methylenedioxy |

TABLE 4-continued

| | | | |
|---|---|---|---|
| 167 | 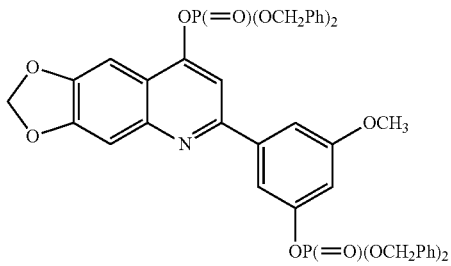 | Dibenzyl 2-(3-([bis-[(benzyl)oxy]] phosphoryl)oxy-5-methoxyphenyl)-6,7-methylenedioxy-quinolin-4-yl phosphate | R = P(=O)(O-benzyl)$_2$<br>$R_5'$ = methoxy<br>$R_6'$, $R_4'$, $R_5$, $R_2$ = H<br>$R_4$, $R_3$ = methylenedioxy<br>$R_3'$ = OP(=O)(O-benzyl)$_2$ |
| 168 | 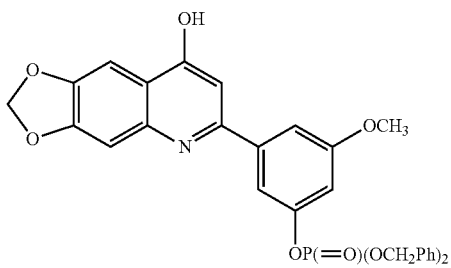 | 2-(3-([bis-[(benzyl)oxy]] phosphoryl)oxy)-5-methoxyphenyl)-6,7-methylenedioxy-quinolin-4-one | R = hydroxy<br>$R_5'$ = methoxy<br>$R_6'$, $R_4'$, $R_2'$, $R_5$, $R_2$ = H<br>$R_4$, $R_3$ = methylenedioxy<br>$R_3'$ = OP(=O)(O-benzyl)$_2$ |
| 169 | 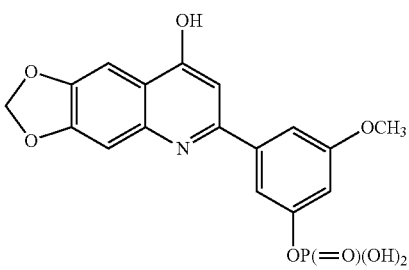 | 2-(3-(dihydrogen) phosphate-5-methoxyphenyl)-6,7-methylenedioxy-quinolin-4-one | $R_5'$ = hydroxy<br>$R_5'$ = methoxy<br>$R_6'$, $R_4'$, $R_2'$, $R_5$, $R_2$ = H<br>$R_4$, $R_3$ = methylenedioxy<br>$R_3'$ = OP(=O)(OH)$_2$ |
| JMC-1 | 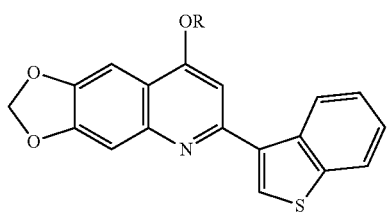 | 2-(3-Benzo[b]thienyl)-6,7-methylenequinolin-4-one | R = H<br>W = benzo[b]thiophen-3-yl<br>$R_5$, $R_2$ = H<br>$R_4$, $R_3$ = methylenedioxy |
| JMC-36 | 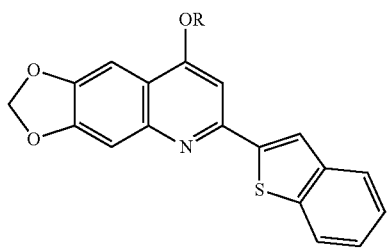 | 2-(2-Benzo[b]thienyl)-6,7-methylene-dioxyquinolin-4-one | R = H<br>W = benzo[b]thiophen-2-yl<br>R, $R_2$ = H<br>$R_4$, $R_3$ = methylenedioxy |
| JMC-38 | 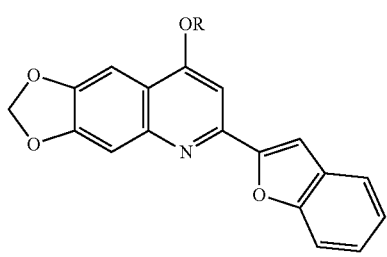 | 2-(2-Benzo[b]furyl)-6,7-methylene-dioxyquinolin-4-one | R = H<br>W = benzo[b]furan-2-yl<br>$R_4$, $R_3$ = methylenedioxy<br>$R_5$, $R_2$ = H |

TABLE 4-continued

| | | | |
|---|---|---|---|
| JMC-40 | 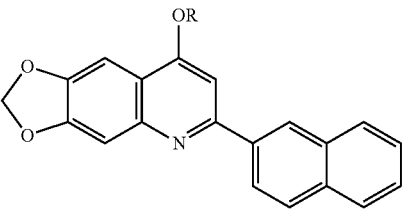 | 2-(2-Naphthalenyl)-6,7-methylenedioxy-quinolin-4-one | R = H<br>W = naphtha-2-yl<br>$R_5, R_2$ = H<br>$R_4$ and $R_3$ = methylenedioxy |
| JMC-41 | 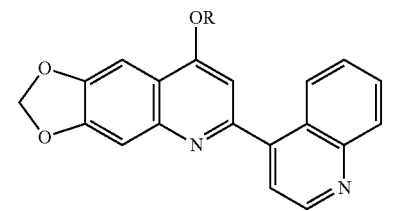 | 2-(4-Quinolinyl)-6,7-methylenedioxy-quinolin-4-one | R = H<br>W = quinolin-4-yl<br>$R_5, R_2$ = H<br>$R_4, R_3$ = methylenedioxy |
| JMC-42 | 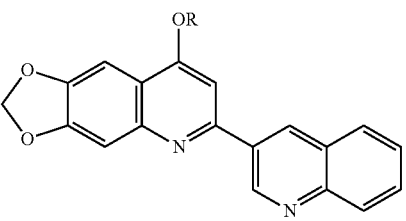 | 2-(3-Quinolinyl)-6,7-methylenedioxy-quinolin-4-one | R = H<br>W = quinolin-3-yl<br>$R_5, R_2$ = H<br>$R_4, R_3$ = methylenedioxy |
| JMC-43 | 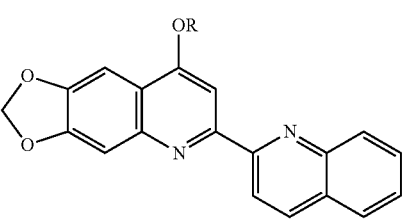 | 2-(2-Quinolinyl)-6,7-methylenedioxy-quinolin-4-one | R = H<br>W = quinolin-2-yl<br>$R_5, R_2$ = H<br>$R_4, R_3$ = methylenedioxy |
| JMC-44 | 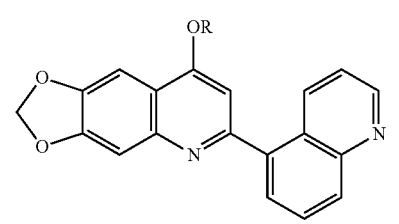 | 2-(5-Quinolinyl)-6,7-methylenedioxy-quinolin-4-one | R = H<br>W = quinolin-5-yl<br>$R_5, R_2$ = H<br>$R_4, R_3$ = methylenedioxy |
| JMC-45 | 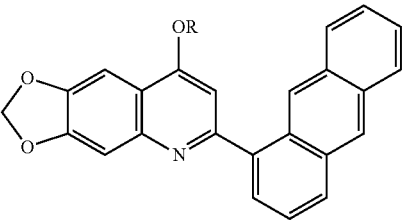 | 2-(1-Anthracenyl)-6,7-methylenedioxy-quinolin-4-one | R = H<br>W = anthracen-1-yl<br>$R_5, R_2$ = H<br>R4, $R_3$ = methylenedioxy |
| CHM-2133 | 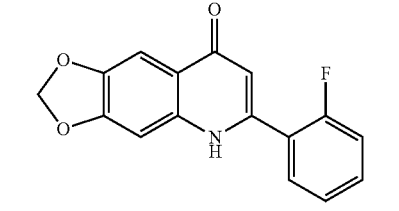 | 2-(2-fluorophenyl)-6,7-methylenedioxy-quinolin-4-one | $R_5', R_4', R_3', R_2'$ = H<br>$R_6'$ = F<br>$R_4$, R3 = methylenedioxy<br>$R_3, R_2$ = H |

TABLE 5

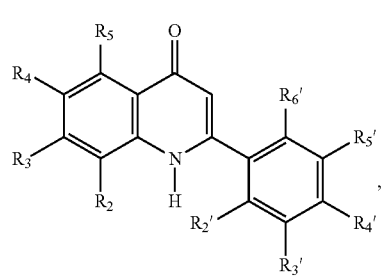

The present invention is not limited to the particular forms as illustrated, and that all the modifications not departing from the spirit and scope of the present invention are within the scope as defined in the appended claims. The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for inhibiting vasculogenic mimicry associated with a metastatic tumor, comprising administering to a subject in need thereof a therapeutically effective amount of a compound of Formula I:

I or a pharmaceutically acceptable salt thereof,
wherein
$R_2'$, $R_3'$, $R_4'$, $R_5'$ and $R_6'$ independently are H, —$(CH_2)_n$YH, Y$(CH_2)_n$CH$_3$, —or X, or $R_5'$ is —O—P(=O)(OH)$_2$ or —OP(=O)(O-benzyl)$_2$,
wherein n is an integer of 0-4, Y is O, X is F, Cl, or Br;
$R_2$, $R_3$, $R_4$ and $R_5$ independently are H, $(CH_2)_n$YH, Y$(CH_2)_n$CH$_3$, X, $(CH_2)_n$NR$_8$R$_9$, $(CH_2)_n$N, or $R_4$ and $R_5$ together is —Y$(CH_2)_n$Y—, or $R_3$ and $R_4$ together is —Y$(CH_2)_n$Y—, or $R_5$ is —O—P(=O)(OH)$_2$ or —O—P(=O)(OCH$_2$Ph)$_2$, wherein n, Y, X, are as defined above, and $R_8$ and $R_9$ independently are $(CH_2)_n$CH$_3$.

2. The method of claim 1, wherein one of $R_2'$, $R_3'$, $R_4'$, $R_5'$ and $R_6'$, is F, or OCH$_3$.

3. The method of claim 1, wherein one of $R_2$, $R_3$, $R_4$, and $R_5$ is Y$(CH_2)_n$CH$_3$ or $(CH_2)_n$NR$_8$R$_9$, and the others thereof are H; or $R_2$ and $R_5$ are H, and $R_3$ and $R_4$ together is —O(CH$_2$)O—.

4. The method of claim 3, wherein $R_2$ and $R_5$ are H, and $R_3$ and $R_4$ together is —O(CH$_2$)O—; and $R_2'$, $R_3'$, $R_4'$ and $R_5'$ are all H, and $R_6'$ is F.

5. The method of claim 3, wherein $R_2$ and $R_5$ are H, and $R_3$ and $R_4$ together is —O(CH$_2$)O—; and $R_2'$, $R_3'$, $R_4'$ and $R_6'$ are all H, and $R_5'$ is F.

6. The method of claim 1, wherein the compound is at least one selected from the group consisting of:

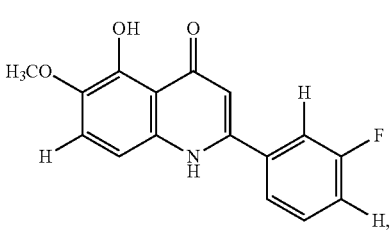

43

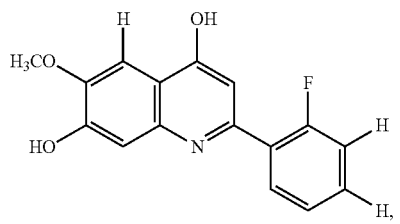

52

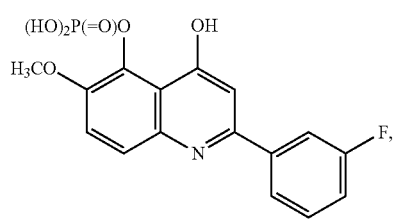

147

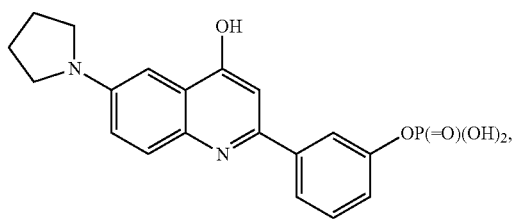

A6

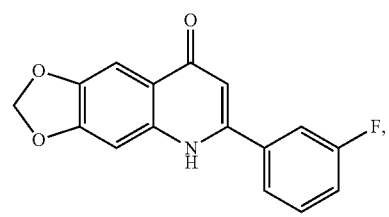

B1

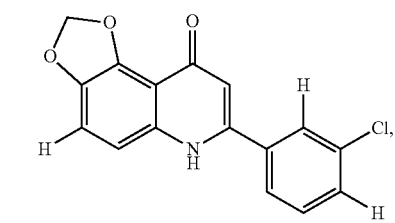

B3

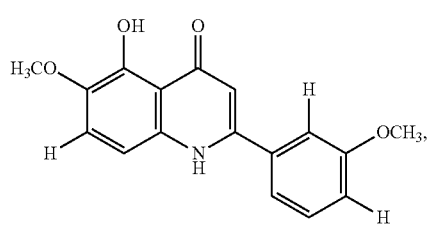

C4

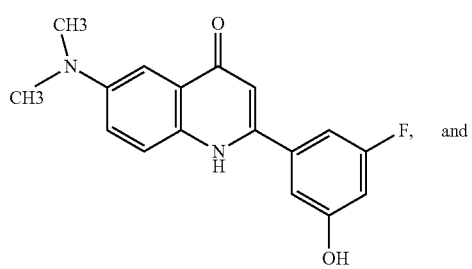

C6

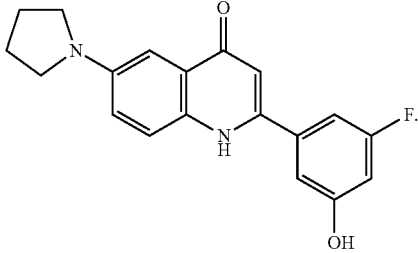

7. The method of claim 1, wherein the metastatic tumor is at least one selected from the group consisting of melanoma, ovarian cancer, prostate cancer, renal cell carcinoma, Ewing sarcoma, breast cancer, neuroendocrine carcinoma, thyroid carcinoma, laryngeal squamous cell carcinoma, hepatocellular carcinoma, uveal melanoma, cutaneous melanoma, oral malignant melanoma, choriocarcinoma, primary gallbladder cancer, malignant esophageal stromal carcinoma, mesothelial sarcoma, alveolar rhabdomyosarcoma, bladder cancer, osteosarcoma, astrocytoma, pheochromocytoma, colorectal cancer, medulloblastoma, adenocarcinoma, esophageal stromal tumors, laryngeal cancer, leukemia, synoviosarcoma, glioblastoma, and gastrointestinal cancer.

8. The method of claim 1, further comprising administering to the subject a therapeutic agent selected from the group consisting of anti-cancer agents, anti-inflammatory agents, anti-proliferative agents, anti-hormonal agents, and any combination thereof.

9. The method of claim 1, wherein the compound is selected from the group consisting of:

16

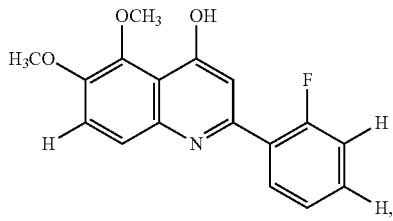

17

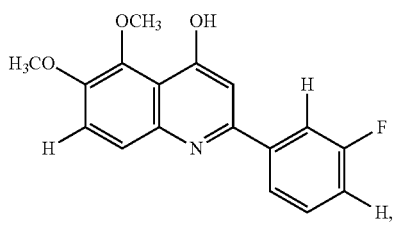

18

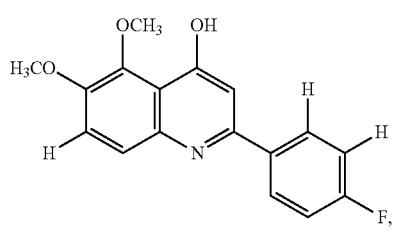

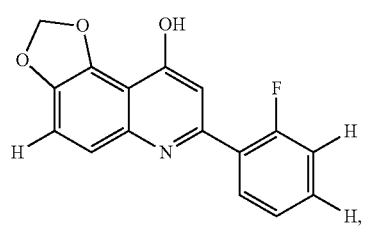 19
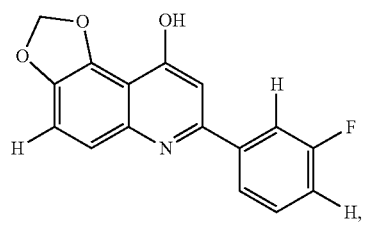 20
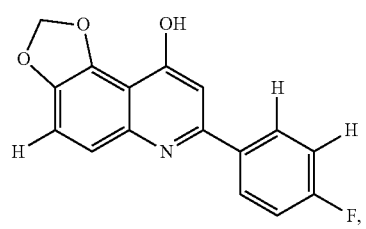 21
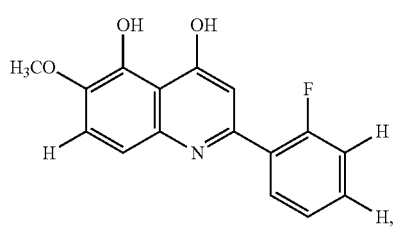 37
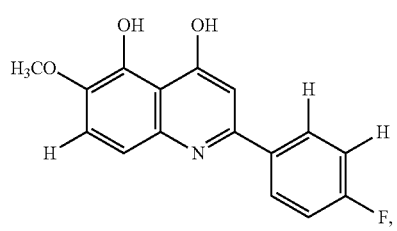 39
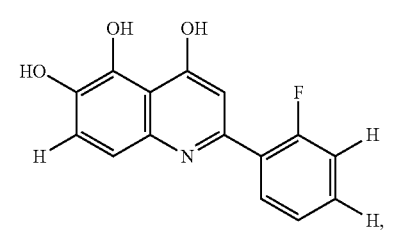 40
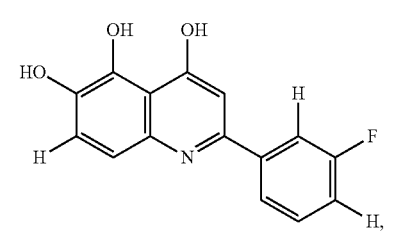 41
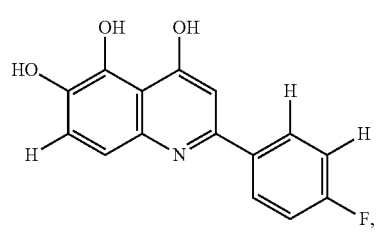 42
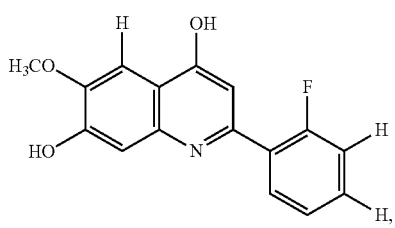 43
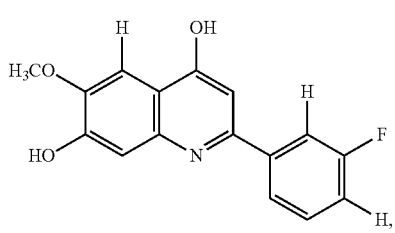 44
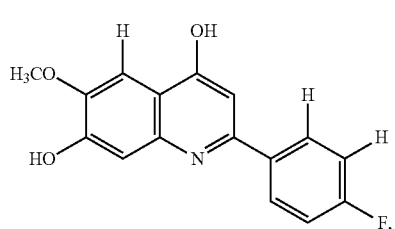 45
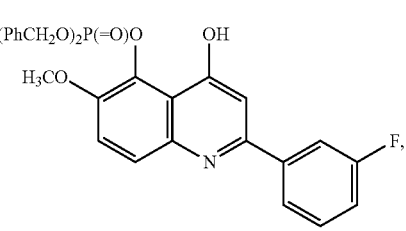 51
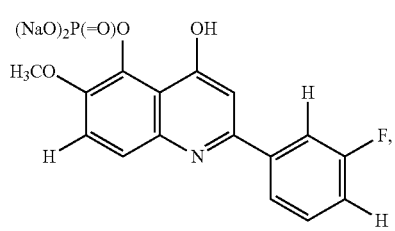 53
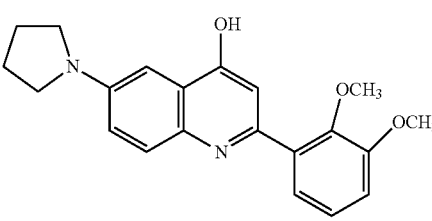 127

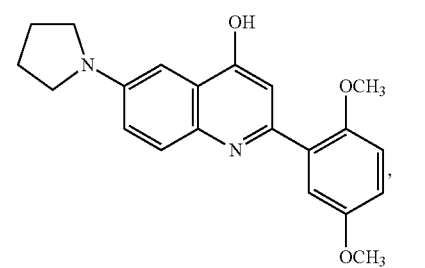
129
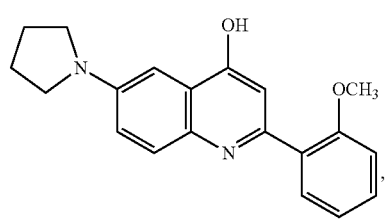
131
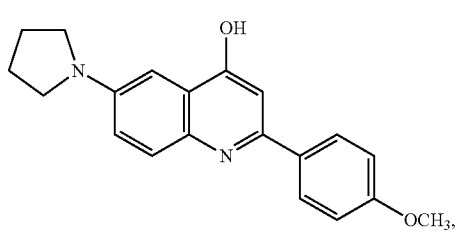
133
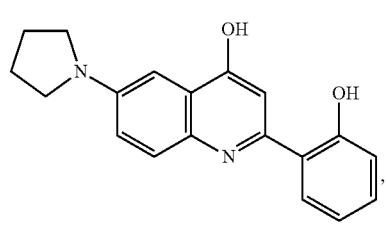
135
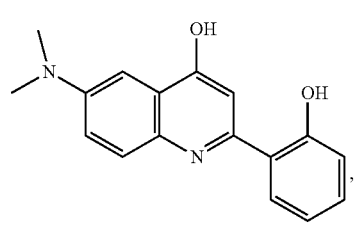
136
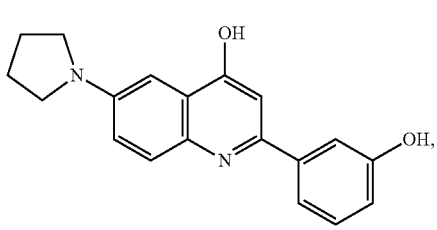
138
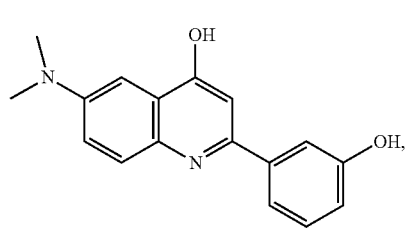
139
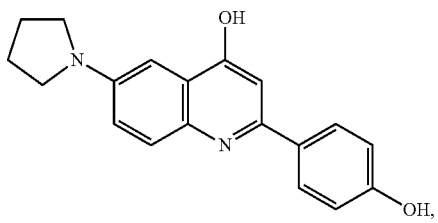
141
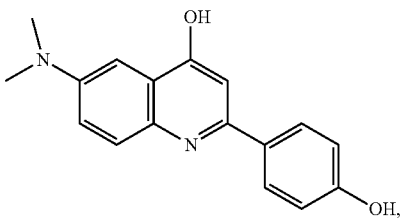
142
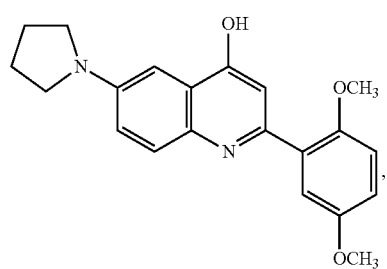
143b
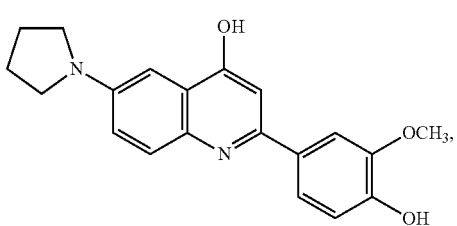
144
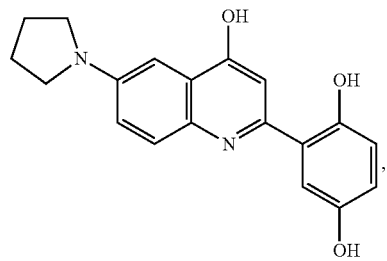
144b
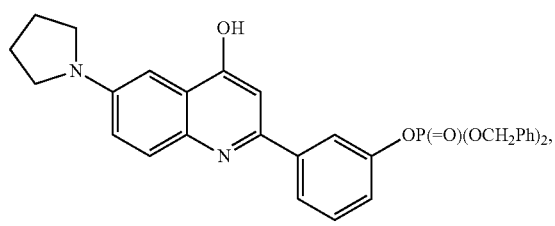
146
and

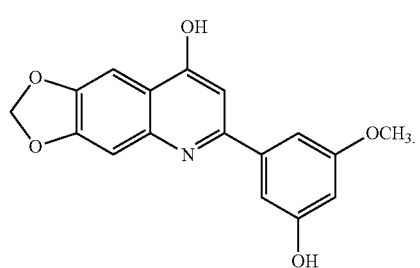
166
* * * * *